(12) United States Patent
Cordoba et al.

(10) Patent No.: US 11,434,293 B2
(45) Date of Patent: *Sep. 6, 2022

(54) ANTI TRBC1 ANTIGEN BINDING DOMAINS

(71) Applicant: AUTOLUS LIMITED, London (GB)

(72) Inventors: Shaun Cordoba, London (GB); Simon Thomas, London (GB); Shimobi Onuoha, London (GB); Ram Jha, London (GB); Wen Chean Lim, London (GB)

(73) Assignee: AUTOLUS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/499,687

(22) Filed: Oct. 12, 2021

(65) Prior Publication Data

US 2022/0098300 A1 Mar. 31, 2022

Related U.S. Application Data

(63) Continuation of application No. 16/620,370, filed as application No. PCT/GB2018/051570 on Jun. 8, 2018.

(30) Foreign Application Priority Data

Jun. 9, 2017 (GB) .................................... 1709203

(51) Int. Cl.
| | | |
|---|---|---|
| C07K 16/28 | (2006.01) | |
| A61K 35/17 | (2015.01) | |
| C07K 14/725 | (2006.01) | |
| C12N 5/0783 | (2010.01) | |
| A61K 47/68 | (2017.01) | |
| C12N 15/86 | (2006.01) | |

(52) U.S. Cl.
CPC .......... *C07K 16/2809* (2013.01); *A61K 35/17* (2013.01); *A61K 47/6803* (2017.08); *A61K 47/6849* (2017.08); *C07K 14/7051* (2013.01); *C12N 5/0636* (2013.01); *C12N 15/86* (2013.01); *C07K 2317/24* (2013.01); *C07K 2317/56* (2013.01); *C07K 2317/622* (2013.01); *C12N 2740/10043* (2013.01)

(58) Field of Classification Search
CPC ............ C07K 16/2809; C07K 14/7051; C12N 5/0636

See application file for complete search history.

(56) References Cited

U.S. PATENT DOCUMENTS

| | | |
|---|---|---|
| 2017/0066827 A1 | 3/2017 | Pule et al. |
| 2017/0334998 A1 | 11/2017 | Pule et al. |
| 2019/0209612 A1 | 7/2019 | Pule et al. |
| 2020/0140549 A1* | 5/2020 | Cordoba ............ C07K 16/2809 |
| 2020/0200756 A1 | 6/2020 | Pule et al. |

FOREIGN PATENT DOCUMENTS

| | | |
|---|---|---|
| CL | 2016002195 A1 | 5/2017 |
| RU | 2355703 C2 | 5/2009 |
| WO | WO-03/093318 A1 | 11/2003 |
| WO | WO-2013/074916 A1 | 5/2013 |
| WO | WO-201 3/153391 A1 | 10/2013 |
| WO | WO-2015/132598 A1 | 9/2015 |
| WO | WO-2015/150771 A1 | 10/2015 |
| WO | WO-2016/030691 A1 | 3/2016 |
| WO | WO-2016/124930 A1 | 8/2016 |
| WO | WO-2016/135470 A1 | 9/2016 |

OTHER PUBLICATIONS

Hogenesch et al., "Challenges in pre-clinical testing of anti-cancer drugs in cell culture and in animal models," J Control Release 164(2):18-186 (2012).

International Search Report and Written Opinion from International Application No. PCT/GB2018/051570 dated Aug. 7, 2018.

Mariuzza, "The Structural Basis of Antigen-Antibody Recognition," Ann. Rev. Biophys. Biophys. Chem., 16:139-159(1987).

McConnell et al., "A general approach to antibody thermostabilization," mAbs 6(5):1274-1282 (2014).

Tang et al., "Immunotherapy and tumor microenvironment," Cancer Letters 370:85-90 (2016).

\* cited by examiner

*Primary Examiner* — Jessica H Roark
(74) *Attorney, Agent, or Firm* — Marshall, Gerstein & Borun LLP

(57) ABSTRACT

The present disclosure relates to anti-TRBC1 antigen binding domains characterized by the sequences of the variable chains. The CDRs sequences of the variable chains are: (VH CDR1) GYTFT, (VH CDR2) NPYNDDIQS, (VH CDR3) GAGYNFDGAYRFFDF; and (VL CDR1) RSSQRLVHSNGNTYL, (VL CDR2) RVSNRFP, (VL CDR3) SQSTHVPYT. The claimed humanized antibodies derive from the murine JOVI antibody. Uses in cancer therapy.

10 Claims, 15 Drawing Sheets

Specification includes a Sequence Listing.

FIGURE 3

| | | | |
|---|---|---|---|
| TRBC1 | 1 | DLNKVFPPEVAVFEPSEAEISHTQKATLVCLATGFFPDHVELSWWVNGKEVHSGVSTDPQ | SEQ ID NO: 35 |
| TRBC2 | 1 | DLKNVFPPEVAVFEPSEAEISHTQKATLVCLATGFYPDHVELSWWVNGKEVHSGVSTDPQ | SEQ ID NO: 36 |
| TRBC1 | 61 | PLKEQPALNDSRYCLSSRLRVSATFWQNPRNHFRCQVQFYGLSENDEWTQDRAKPVTQIV | SEQ ID NO: 35 |
| TRBC2 | 61 | PLKEQPALNDSRYCLSSRLRVSATFWQNPRNHFRCQVQFYGLSENDEWTQDRAKPVTQIV | SEQ ID NO: 36 |
| TRBC1 | 121 | SAEAWGRADCGFTSVSYQQGVLSATILYEILLGKATLYAVLVSALVLMAMVKRKD | SEQ ID NO: 35 |
| TRBC2 | 121 | SAEAWGRADCGFTSESYQQGVLSATILYEILLGKATLYAVLVSALVLMAMVKRKD | SEQ ID NO: 36 |

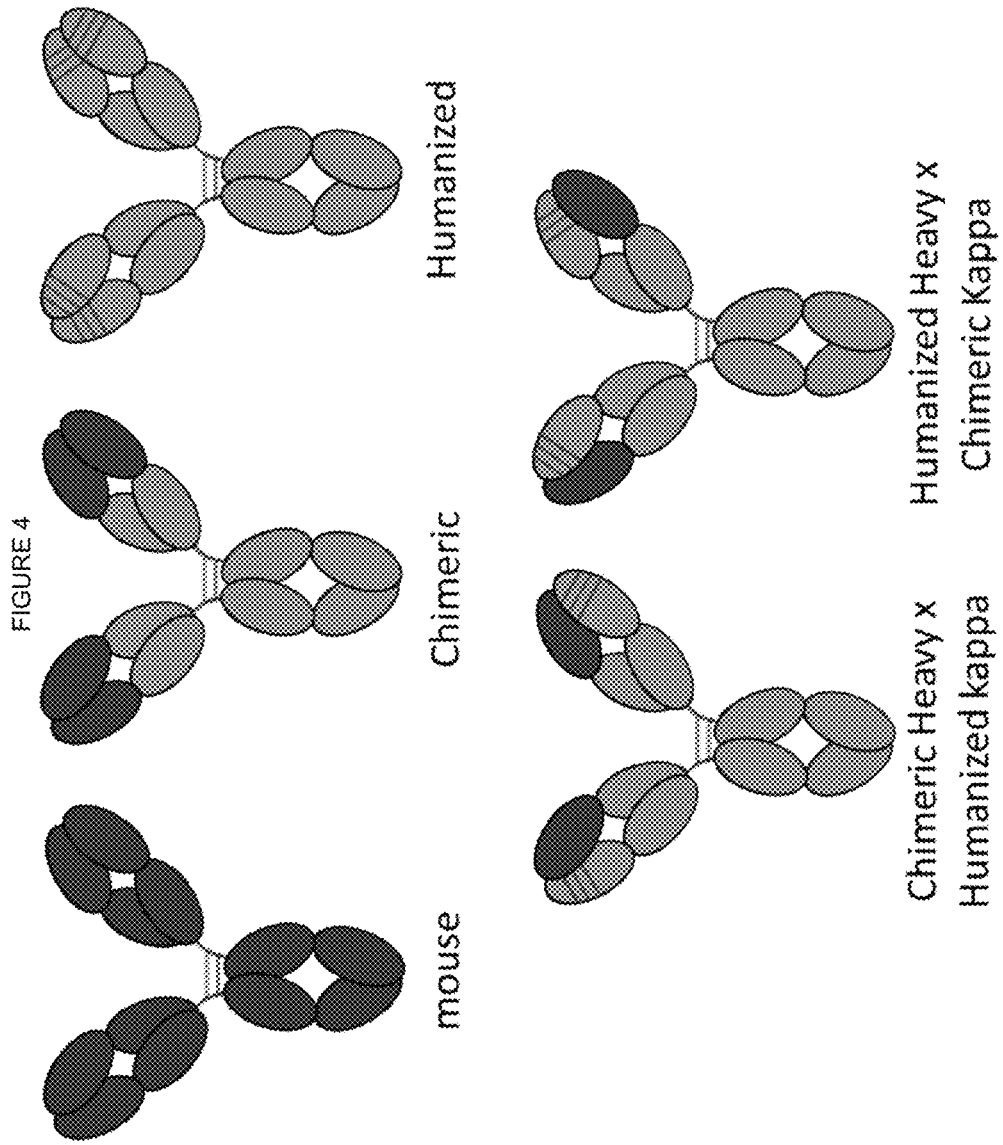

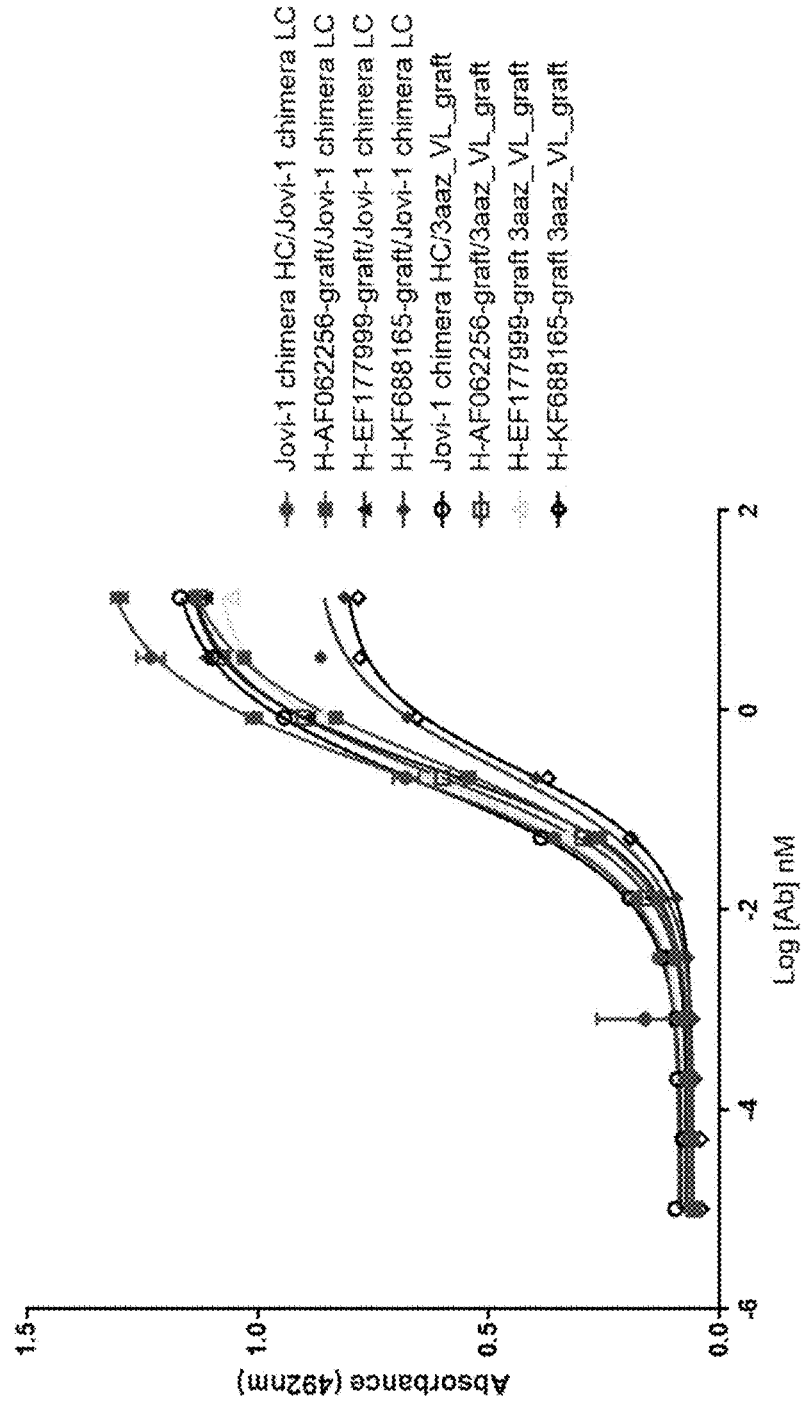

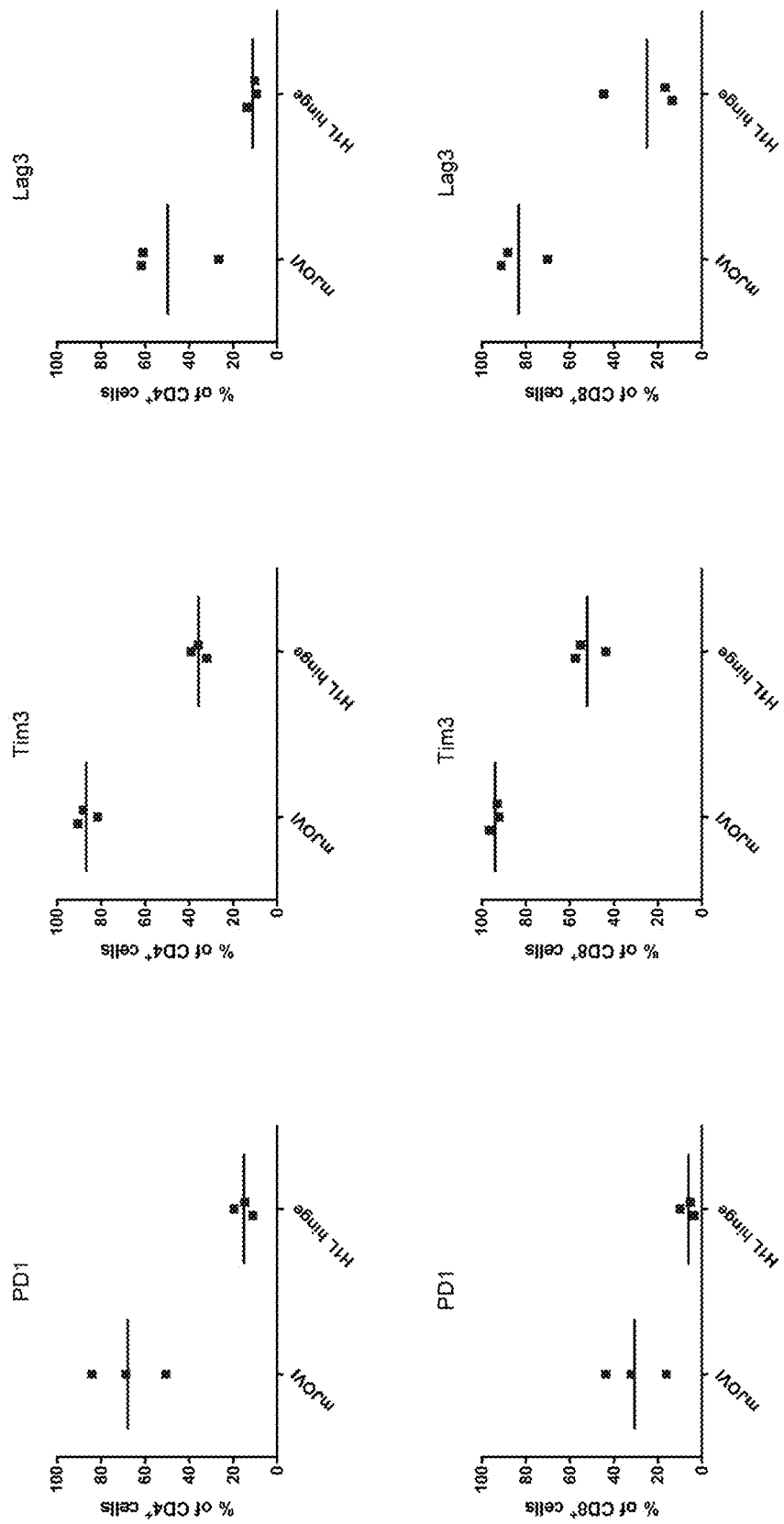

ANTI TRBC1 ANTIGEN BINDING DOMAINS

CROSS-REFERENCE TO RELATED APPLICATIONS

This is a Continuation of U.S. application Ser. No. 16/620,370, filed Dec. 6, 2019, which is a U.S. National Phase of International Application No. PCT/GB2018/051570, filed Jun. 8, 2018, which claims priority to Great Britain Application No. 1709203.2, filed Jun. 9, 2017.

INCORPORATION BY REFERENCE OF THE SEQUENCE LISTING

This application contains, as a separate part of disclosure, a Sequence Listing in computer-readable form (filename 53688A_Seqlisting.text; 36,126 bytes—ASCII text file created Sep. 9, 2021) which is incorporated by reference herein in its entirety.

FIELD OF THE INVENTION

The present invention relates to agents useful in the treatment of T-cell lymphoma or leukaemia.

BACKGROUND TO THE INVENTION

Lymphoid malignancies can largely be divided into those which are derived from either T-cells or B-cells. T-cell malignancies are a clinically and biologically heterogeneous group of disorders, together comprising 10-20% of non-Hodgkin's lymphomas and 20% of acute leukaemias. The most commonly identified histological subtypes are peripheral T-cell lymphoma, not otherwise specified (PTCL-NOS); angio-immunoblastic T-cell lymphoma (AITL) and anaplastic large cell lymphoma (ALCL). Of all acute Lymphoblastic Leukaemias (ALL), some 20% are of a T-cell phenotype.

These conditions typically behave aggressively, compared for instance with B-cell malignancies, with estimated 5-year survival of only 30%. In the case of T-cell lymphoma, they are associated with a high proportion of patients presenting with disseminated disease, unfavourable International Prognostic Indicator (IPI) score and prevalence of extra-nodal disease. Chemotherapy alone is not usually effective and less than 30% of patients are cured with current treatments.

Further, unlike in B-cell malignancies, where immunotherapies such as the anti-CD20 monoclonal antibody rituximab have dramatically improved outcomes, there is currently no equivalently effective, minimally toxic immunotherapeutic available for the treatment of T-cell malignancies. An important difficulty in the development of immunotherapy for T-cell disorders is the considerable overlap in marker expression of clonal and normal T-cells, with no single antigen clearly able to identify clonal (malignant) cells.

The same problem exists when targeting a pan-B-cell antigen to treat a B-cell malignancy. However, in this case, the concomitant depletion of the B-cell compartment results in relatively minor immunosuppression which is readily tolerated by most patients. Further, in therapies which result in particularly long-term depletion of the normal B-compartment, its loss can be largely abrogated by administration of pooled immunoglobulin. The situation is completely different when targeting T-cell malignancies. Here, concomitant depletion of the T-cell compartment leads to severe immunosuppression and severe toxicity. Further, there is no satisfactory way to mitigate loss of the T-cell compartment.

The toxicity is in part illustrated by the clinical effects of the therapeutic monoclonal antibody Alemtuzumab. This agent lyses cells which express CD52 and has some efficacy in T-cell malignancies. The utility of this agent is greatly limited by a profound cellular immunodeficiency, largely due to T-cell depletion, with markedly elevated risk of infection.

There is thus a need for a new method for targeted treatment of T-cell malignancies which is not associated with the above disadvantages.

DESCRIPTION OF THE FIGURES

FIG. 3: Alignment of human TRBC1 and TRBC2 at the amino acid level. The TCR$\beta$ constant chain coded for by TRBC1 and TRBC2 differ by only 4 amino acid differences: K/N at position 3 of the TRBC; N/K at position 4 of the TRBC; F/Y at position 36 of the TRBC; V/E at position 135 of the TRBC.

FIG. 4: Schematic diagrams illustrating different antibody types referred to in the generation of humanized anti-TRBC1 binders.

FIG. 5: Heavy and light chain graft selection. Humanised VH and VL domains were created comprising the CDRs from JOVI-1 together with various human framework regions. Chimeric antibodies were generated comprising humanized VH with murine VL domains, or humanized VL with muring VH domains and compared with a control chimeric antibody having murine VH and VL (Jovi-1 chimera HC/Jovi-1 chimera LC). Humanised antibodies were also created with humanized VH and VL combinations. All antibodies were tested for binding to TRBC1 by ELISA.

FIG. 14: Expression of exhaustion markers following co-culture with target cells. Activated PBMCs were transduced with the murine JOVI1 CAR (mJOVI) or humanised Jovi-1 CAR (H1L hinge), depleted of CD56-expressing cells and co-cultured with TRBC1-TCR-expressing Raji target cells. After 96 hours, cells were stained with anti-PD1, anti-LAG3 and anti-Tim3 antibodies then analysed by flow cytometry.

SUMMARY OF ASPECTS OF THE INVENTION

Figure 1:
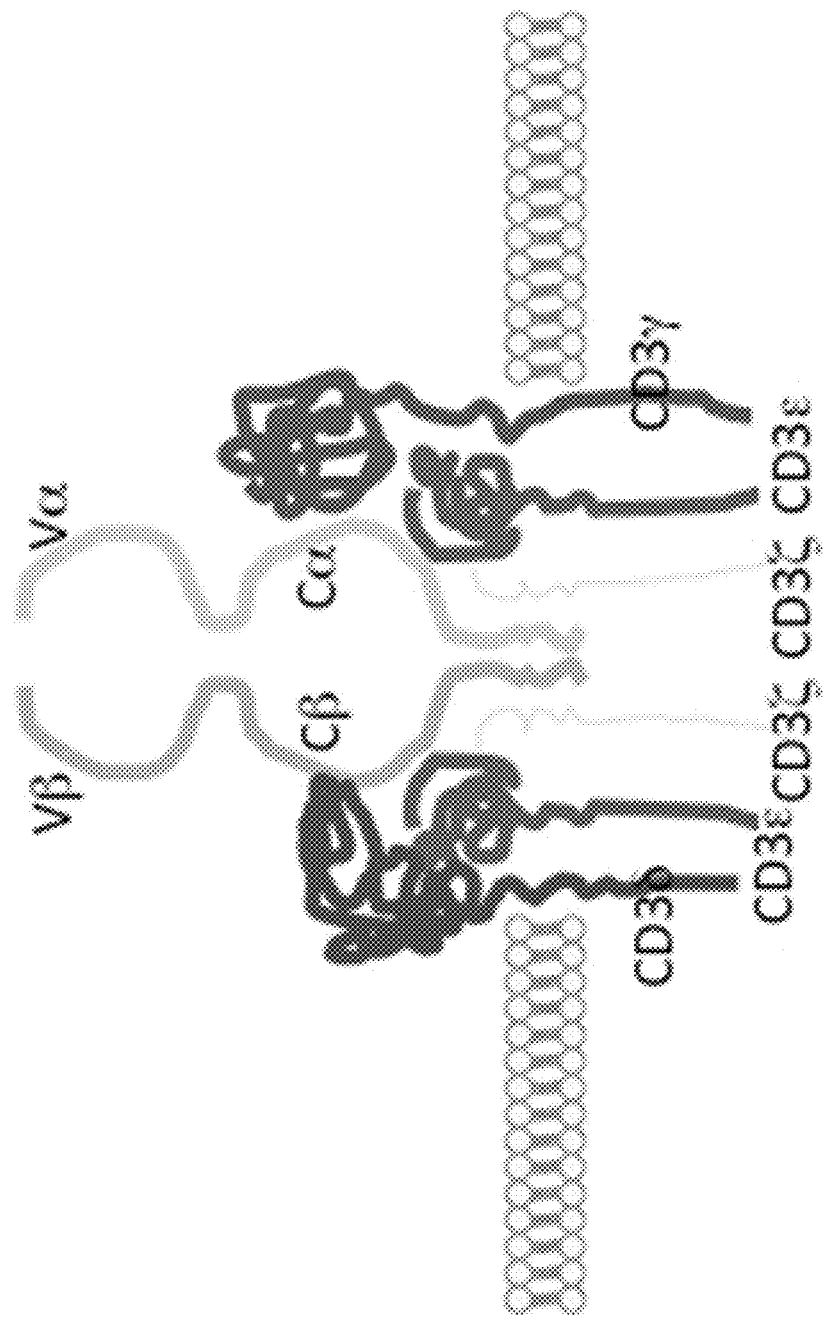
FIG. 1: A diagram of the $\alpha\beta$ T-cell Receptor/CD3 Complex. The T-cell receptor is formed from 6 different protein chains which must assemble in the endoplasmic reticulum to be expressed on the cell surface. The four proteins of the CD3 complex (CD3$\zeta$, CD3$\gamma$, CD3$\epsilon$ and CD3$\delta$) sheath the T-cell Receptor (TCR). This TCR imbues the complex with specificity of a particular antigen and is composed of two chains: TCR$\alpha$ and TCR$\beta$. Each TCR chain has a variable component distal to the membrane and a constant component proximal to the membrane. Nearly all T-cell lymphomas and many T-cell leukaemias express the TCR/CD3 complex.

The present inventors have developed a series of humanised antigen-binding domains which bind human TRBC1. The antigen-binding domain can be used in a variety of therapeutic formats, including a chimeric antigen receptor (CAR), therapeutic antibody, antibody-drug conjugate (ADC) and bi-specific T cell engager (BiTE) to deplete malignant TRBC1-expressing T-cells in a subject, without affecting healthy TRBC2-expressing T cells.

Thus in a first aspect, the invention provides anti-TRBC1 antigen-binding domain which comprises:
  a) a VH domain having an amino acid sequence selected from SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17 and SEQ ID No. 18; and
  b) a VL domain having an amino acid sequence selected from SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34.

In a second aspect, the invention provides a chimeric antigen receptor (CAR) which comprises an anti-TRBC1 antigen binding domain according to the first aspect of the invention.

In a third aspect, the invention provides an antibody which comprises an anti-TRBC1 antigen binding domain according to the first aspect of the invention.

In a fourth aspect, the invention provides a bispecific T-cell engager (BiTE) which comprises an anti-TRBC1 antigen binding domain according to the first aspect of the invention.

In a fifth aspect, the invention provides antibody-drug conjugate which comprises an anti-TRBC1 antigen binding domain according to the first aspect of the invention.

In a sixth aspect, the invention provides a nucleic acid sequence which encodes a CAR according to the second aspect of the invention.

In a seventh aspect, the invention provides a vector comprising a nucleic acid sequence according to the sixth aspect the invention.

In an eighth aspect, the invention provides cell comprising a CAR according to the second aspect of the invention.

In a ninth aspect, the invention provides a method for making a cell according to the eighth aspect of the invention, which comprises the step of introducing a nucleic acid according to the sixth aspect of the invention or a vector according to the seventh aspect of the invention into a cell.

In a tenth aspect, the invention provides a pharmaceutical composition which comprises a plurality of cells according to the eighth aspect of the invention, an antibody according to the third aspect of the invention, a BiTE according to the fourth aspect of the invention or an antibody-drug conjugate according to the fifth aspect of the invention.

In an eleventh aspect, the invention provides a pharmaceutical composition according to the tenth aspect of the invention for use in treating a TRBC1-expressing T-cell lymphoma or leukaemia in a subject.

In a twelfth aspect, the invention provides a method for treating a TRBC1-expressing T-cell lymphoma or leukaemia in a subject, which comprises the step of administering a pharmaceutical composition according to the tenth aspect of the invention to a subject.

In a thirteenth aspect, the invention provides the use of a pharmaceutical composition according to the tenth aspect of the invention in the manufacture of a medicament for treating a TRBC1-expressing T-cell lymphoma or leukaemia in a subject.

The TRBC1-expressing T-cell lymphoma or leukaemia may be selected from: peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

DETAILED DESCRIPTION

The invention provides agents, such as chimeric antigen receptors (CARs) which selectively bind TRBC1. Such agents are useful in methods for treating a T-cell lymphoma or leukaemia in a subject. T cell malignancies are clonal, so they either express TRBC1 or TRBC2. By administering a TCRB1 selective agent to the subject, the agent causes selective depletion of the TRBC1-expressing malignant T-cells, together with TRBC1-expressing normal T-cells, but does not cause depletion of TRBC2-expressing normal T-cells.

TCR β Constant Region (TRBC)

The T-cell receptor (TCR) is expressed on the surface of T lymphocytes and is responsible for recognizing antigens bound to major histocompatibility complex (MHC) molecules. When the TCR engages with antigenic peptide and MHC (peptide/MHC), the T lymphocyte is activated through a series of biochemical events mediated by associated enzymes, co-receptors, specialized adaptor molecules, and activated or released transcription factors.

The TCR is a disulfide-linked membrane-anchored heterodimer normally consisting of the highly variable alpha (α) and beta (β) chains expressed as part of a complex with the invariant CD3 chain molecules. T-cells expressing this receptor are referred to as α:β (or αβ) T-cells (~95% total T-cells). A minority of T-cells express an alternate receptor, formed by variable gamma (γ) and delta (δ) chains, and are referred to as γδ T-cells (~5% total T cells).

Each α and β chain is composed of two extracellular domains: Variable (V) region and a Constant (C) region, both of Immunoglobulin superfamily (IgSF) domain forming antiparallel β-sheets. The constant region is proximal to the cell membrane, followed by a transmembrane region and a short cytoplasmic tail, while the variable region binds to the peptide/MHC complex (see FIG. 1). The constant region of the TCR consists of short connecting sequences in which a cysteine residue forms disulfide bonds, which forms a link between the two chains.

The variable domains of both the TCR α-chain and β-chain have three hypervariable or complementarity determining regions (CDRs). The variable region of the β-chain also has an additional area of hypervariability (HV4), however, this does not normally contact antigen and is therefore not considered a CDR.

The TCR also comprises up to five invariant chains γ, δ, ε (collectively termed CD3) and ζ. The CD3 and ζ subunits mediate TCR signalling through specific cytoplasmic domains which interact with second-messenger and adapter molecules following the recognition of the antigen by αβ or γδ. Cell-surface expression of the TCR complex is preceded by the pair-wise assembly of subunits in which both the transmembrane and extracellular domains of TCR α and β and CD3 γ and δ play a role TCRs are therefore commonly composed of the CD3 complex and the TCR α and β chains, which are in turn composed of variable and constant regions (FIG. 1).

Figure 2:
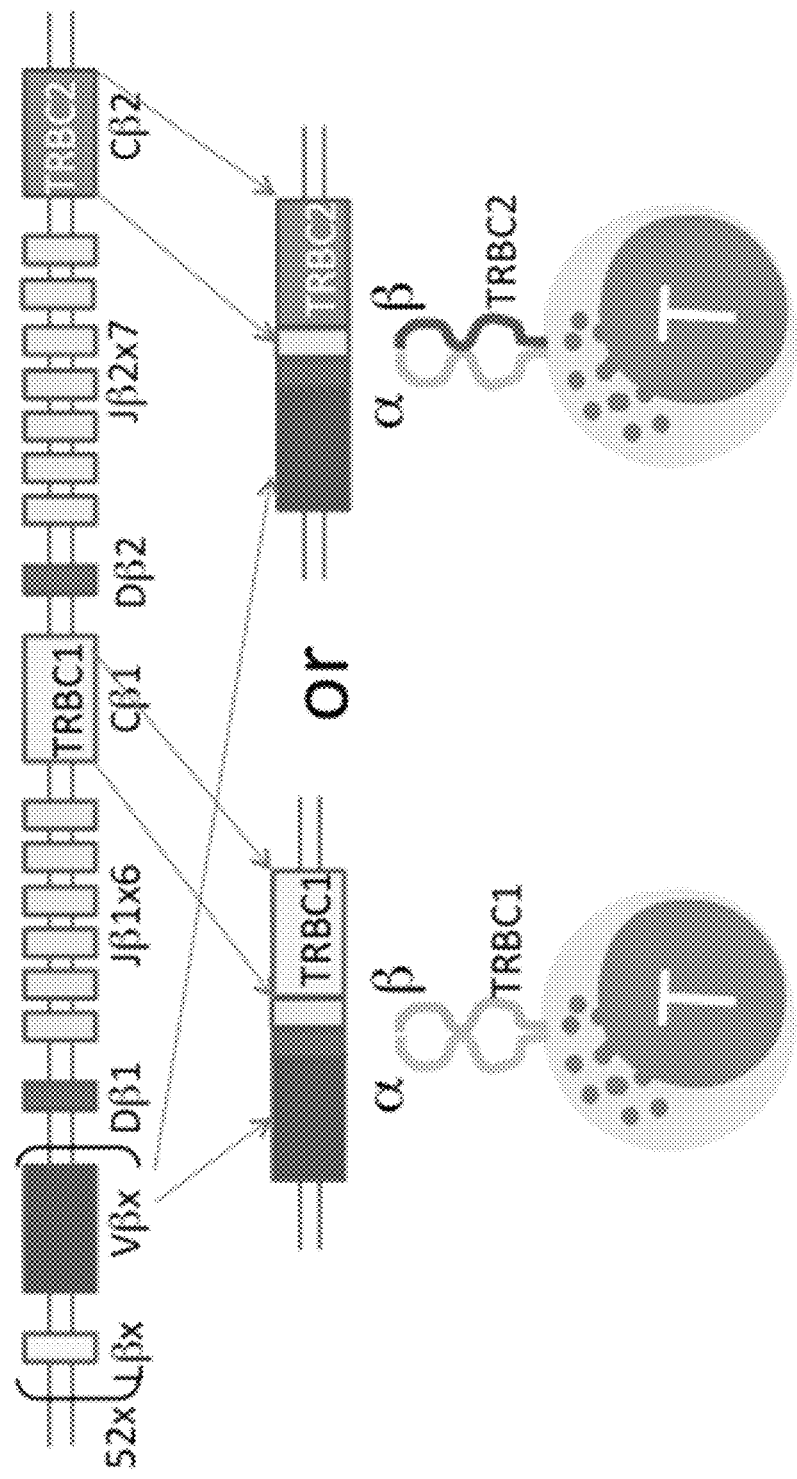
FIG. 2: The segregation of T-cell Receptor $\beta$-constant region (TRBC)-1 and TRBC2 during T-cell receptor rearrangement. Each TCR beta chain is formed from genomic recombination of a particular beta variable (V), diversity (D), joining (J) and constant (TRBC) regions. The human genome contains two very similar and functionally equivalent TRBC loci known as TRBC1 and TRBC2. During TCR gene re-arrangement, a J-region recombines with either TRBC1 or TRBC2. This rearrangement is permanent. T-cells express many copies of a single TCR on their surface, hence each T-cell will express a TCR whose $\beta$-chain constant region is coded for by either TRBC1 or TRBC2.

The locus (Chr7:q34) which supplies the TCR β-constant region (TRBC) has duplicated in evolutionary history to produce two almost identical and functionally equivalent genes: TRBC1 and TRBC2 (FIG. 2), which differ by only 4 amino acid in the mature protein produced by each (FIG. 3). Each TCR will comprise, in a mutually exclusive fashion, either TRBC1 or TRBC2 and as such, each αβ T-cell will express either TRBC1 or TRBC2, in a mutually exclusive manner.

Despite the similarity between the sequence of the TRBC1 and TRBC2, it is possible to discriminate between them. The amino acid sequences of TRBC1 and TRBC2 can be discriminated whilst in situ on the surface of a cell, for example a T-cell.

Antigen Binding Domain

The present invention provides a humanised anti-TRBC1 antigen-binding domain which has a variable heavy chain (VH) and a variable light chain (VL) which comprise the following complementarity determining regions (CDRs):

```
VH CDR1:
                                        (SEQ ID No. 1)
GYTFTGY;

VH CDR2:
                                        (SEQ ID No. 2)
NPYNDD;
```

```
VH CDR3:
                                        (SEQ ID No. 3)
GAGYNFDGAYRFFDF;

VL CDR1:
                                        (SEQ ID No. 4)
RSSQRLVHSNGNTYLH;

VL CDR2:
                                        (SEQ ID No. 5)
RVSNRFP;
and

VL CDR3:
                                        (SEQ ID No. 6)
SQSTHVPYT.
```

The antigen binding domain comprises human framework regions, or human framework regions with one or more mutations. For example the framework region(s) may comprise one or more substitutions compared to the human framework region sequence. The substitutions may be "back-mutations" where one or more amino acids are substituted with the equivalent residue from the murine antibody sequence. The murine antibody variable heavy chain (VH) sequence is shown below as SEQ ID No. 7 and the variable light chain (VL) sequence shown as SEQ ID No. 8. In both sequences, the CDR sequences are in bold and underlined.

```
murine Jovi-1 VH
                                        SEQ ID No. 7
EVRLQQSGPDLIKPGASVKMSCKASGYTFTGYVMHWVKQRPGQGLEWIG
FINPYNDDIQSNERFRGKATLTSDKSSTTAYMELSSLTSEDSAVYYCAR
GAGYNFDGAYRFFDFWGQGTTLTVSS -murine Jovi-1 VL
                                        SEQ ID No. 8
DVVMTQSPLSLPVSLGDQASISCRSSQRLVHSNGNTYLHWYLQKPGQSP
KLLIYRVSNRFPGVPDRFSGSGSGTDFTLKISRVEAEDLGIYFCSQSTH
VPYTFGGGTKLEIKR
```

A humanised VH sequence comprising the murine JOVI-1 CDRs shown as SEQ ID No. 1, 2 and 3 may comprise 6 or fewer, 5 or fewer, 4 or fewer, 3 or fewer, 2 or 1 mutations compared to the wild-type human framework region sequence.

A humanised VL sequence comprising the murine JOVI-1 CDRs shown as SEQ ID No. 4, 5 and 6 may comprise 6 or fewer, 5 or fewer, 4 or fewer, 3 or fewer, 2 or 1 mutation compared to the wild-type human framework region sequence.

The VH sequence may comprise JOVI-1 VH CDRs with the human framework H-AF062256. This sequence is shown as SEQ ID No. 9. The CDR sequences are underlined.

```
-Humanised Jovi-1 H-AF062256 framework
                                        SEQ ID No. 9
QVQLVQSGAEVKKPGASVKVSCKASGYTFTGYVMHWVRQAPGQGLEWMG
FINPYNDDIQSNERFRGRVTMTRDTSISTAYMELSRLRSDDTAVYYCAR
GAGYNFDGAYRFFDFWGQGTMVTVSS
```

The VH sequence may comprise JOVI-1 VH CDRs with the human framework H-EF177999. This sequence is shown as SEQ ID No. 10. The CDR sequences are underlined.

```
-Humanised Jovi-1 H-EF177999 framework
                                        SEQ ID No. 10
EVQLVESGAEVKKPGASVKVSCKASGYTFTGYVMHWVRQAPGQGLEWMG
FINPYNDDIQSNERFRGRVTMTRDTSTSTVYMELSSLRSEDTAVYYCAR
GAGYNFDGAYRFFDFWGQGTLVTVSS
```

The VH sequence may comprise JOVI-1 VH CDRs with the human framework H-KF688165. This sequence is shown as SEQ ID No. 11. The CDR sequences are underlined.

```
-Humanised Jovi-1 H- H-KF688165 framework
                                    SEQ ID No. 11
QVQLVQSGAEVKKPGASVKVSCKASEYSFTGYVMHWVRQAPGQGLEWMG
FINPYNDDIQSNERFRGRVTMTRDTSISTAYMEVSSLTSDDAAIYYCAR
GAGYNFDGAYRFFDFWGQGTLVTVSS
```

The VH sequence may comprise the sequence shown as SEQ ID No. 9, 10 or 11 with one or more mutations, such as back-mutations. The VH sequence may comprise 6 or fewer, 5 or fewer, 4 or fewer, 3 or fewer, 2 or 1 mutation compared to the wild-type human framework region sequence. For example, the VH sequence may comprise the sequence shown as SEQ ID No. 9 with one of the sets of back-mutations shown in Table 1 in the Examples.

The VH sequence may comprise one of the sequences shown as SEQ ID No. 12 to 18. The CDR sequences are underlined and back-mutations are shown in bold.

```
-mutation K73
                                    SEQ ID No. 12
QVQLVQSGAEVKKPGASVKVSCKASGYTFTGYVMHWVRQAPGQGLEWMG
FINPYNDDIQSNERFRGRVTMTRDKSISTAYMELSRLRSDDTAVYYCAR
GAGYNFDGAYRFFDFWGQGTMVTVSS -mutation S71
                                    SEQ ID No. 13
QVQLVQSGAEVKKPGASVKVSCKASGYTFTGYVMHWVRQAPGQGLEWMG
FINPYNDDIQSNERFRGRVTMTSDTSISTAYMELSRLRSDDTAVYYCAR
GAGYNFDGAYRFFDFWGQGTMVTVSS -mutations S71, K73
                                    SEQ ID No. 14
QVQLVQSGAEVKKPGASVKVSCKASGYTFTGYVMHWVRQAPGQGLEWMG
FINPYNDDIQSNERFRGRVTMTSDKSISTAYMELSRLRSDDTAVYYCAR
GAGYNFDGAYRFFDFWGQGTMVTVSS -mutation I48
                                    SEQ ID No. 15
QVQLVQSGAEVKKPGASVKVSCKASGYTFTGYVMHWVRQAPGQGLEWIG
FINPYNDDIQSNERFRGRVTMTRDTSISTAYMELSRLRSDDTAVYYCAR
GAGYNFDGAYRFFDFWGQGTMVTVSS -mutation I48, K73
                                    SEQ ID No. 16
QVQLVQSGAEVKKPGASVKVSCKASGYTFTGYVMHWVRQAPGQGLEWIG
FINPYNDDIQSNERFRGRVTMTRDKSISTAYMELSRLRSDDTAVYYCAR
GAGYNFDGAYRFFDFWGQGTMVTVSS -mutations M20, S71, K73
                                    SEQ ID No. 17
QVQLVQSGAEVKKPGASVKMSCKASGYTFTGYVMHWVRQAPGQGLEWMG
FINPYNDDIQSNERFRGRVTMTSDKSISTAYMELSRLRSDDTAVYYCAR
GAGYNFDGAYRFFDFWGQGTMVTVSS -mutations M20, I48
                                    SEQ ID No. 18
QVQLVQSGAEVKKPGASVKMSCKASGYTFTGYVMHWVRQAPGQGLEWIG
FINPYNDDIQSNERFRGRVTMTRDTSISTAYMELSRLRSDDTAVYYCAR
GAGYNFDGAYRFFDFWGQGTMVTVSS
```

The VL sequence may comprise JOVI-1 VL CDRs with the human framework 3aaz. This sequence is shown as SEQ ID No. 19. The CDR sequences are underlined.

```
                                    SEQ ID No. 19
DIVMTQSPLSLPVTPGEPASISCRSSQRLVHSNGNTYLHWYLQKPGQSP
RLLIYRVSNRFPGVPDRFSGSGSGTDFTLKISRVEAEDVGVYYCSQSTH
VPYTFGQGTKLEIK
```

The VL sequence may comprise the sequence shown as SEQ ID No. 19 with one or more mutations, such as back-mutations. The VL sequence may comprise 6 or fewer, 5 or fewer, 4 or fewer, 3 or fewer, 2 or 1 mutation compared to the wild-type human framework region sequence. For example, the VL sequence may comprise one of the sequences shown as SEQ ID No. 20 to 34. The CDR sequences are underlined and back-mutations are shown in bold.

```
                                    SEQ ID No. 20
DIVMTQSPLSLPVTLGEQASISCRSSQRLVHSNGNTYLHWYLQKPGQSP
RLLIYRVSNRFPGVPDRFSGSGSGTDFTLKISRVEAEDVGVYFCSQSTH
VPYTFGGGTKLEIK

SEQ ID No. 21
DIVMTQSPLSLPVTLGEQASISCRSSQRLVHSNGNTYLHWYLQKPGQSP
RLLIYRVSNRFPGVPDRFSGSGSGTDFTLKISRVEAEDVGVYFCSQSTH
VPYTFGQGTKLEIK

SEQ ID No. 22
DIVMTQSPLSLPVTLGEQASISCRSSQRLVHSNGNTYLHWYLQKPGQSP
RLLIYRVSNRFPGVPDRFSGSGSGTDFTLKISRVEAEDVGVYYCSQSTH
VPYTFGGGTKLEIK

SEQ ID No. 23
DIVMTQSPLSLPVTLGEQASISCRSSQRLVHSNGNTYLHWYLQKPGQSP
RLLIYRVSNRFPGVPDRFSGSGSGTDFTLKISRVEAEDVGVYYCSQSTH
VPYTFGQGTKLEIK

SEQ ID No. 24
DIVMTQSPLSLPVTLGEPASISCRSSQRLVHSNGNTYLHWYLQKPGQSP
RLLIYRVSNRFPGVPDRFSGSGSGTDFTLKISRVEAEDVGVYFCSQSTH
VPYTFGGGTKLEIK

SEQ ID No. 25
DIVMTQSPLSLPVTLGEPASISCRSSQRLVHSNGNTYLHWYLQKPGQSP
RLLIYRVSNRFPGVPDRFSGSGSGTDFTLKISRVEAEDVGVFYCSQSTH
VPYTFGQGTKLEIK

SEQ ID No. 26
DIVMTQSPLSLPVTLGEPASISCRSSQRLVHSNGNTYLHWYLQKPGQSP
RLLIYRVSNRFPGVPDRFSGSGSGTDFTLKISRVEAEDVGVYYCSQSTH
VPYTFGGGTKLEIK

SEQ ID No. 27
DIVMTQSPLSLPVTLGEPASISCRSSQRLVHSNGNTYLHWYLQKPGQSP
RLLIYRVSNRFPGVPDRFSGSGSGTDFTLKISRVEAEDVGVYYCSQSTH
VPYTFGQGTKLEIK

SEQ ID No. 28
DIVMTQSPLSLPVTPGEQASISCRSSQRLVHSNGNTYLHWYLQKPGQSP
RLLIYRVSNRFPGVPDRFSGSGSGTDFTLKISRVEAEDVGVYFCSQSTH
VPYTFGGGTKLEIK

SEQ ID No. 29
DIVMTQSPLSLPVTPGEQASISCRSSQRLVHSNGNTYLHWYLQKPGQSP
RLLIYRVSNRFPGVPDRFSGSGSGTDFTLKISRVEAEDVGVYFCSQSTH
VPYTFGQGTKLEIK

SEQ ID No. 30
DIVMTQSPLSLPVTPGEQASISCRSSQRLVHSNGNTYLHWYLQKPGQSP
RLLIYRVSNRFPGVPDRFSGSGSGTDFTLKISRVEAEDVGVYYCSQSTH
VPYTFGGGTKLEIK

SEQ ID No. 31
DIVMTQSPLSLPVTPGEQASISCRSSQRLVHSNGNTYLHWYLQKPGQSP
RLLIYRVSNRFPGVPDRFSGSGSGTDFTLKISRVEAEDVGVYYCSQSTH
VPYTFGQGTKLEIK

SEQ ID No. 32
DIVMTQSPLSLPVTPGEPASISCRSSQRLVHSNGNTYLHWYLQKPGQSP
RLLIYRVSNRFPGVPDRFSGSGSGTDFTLKISRVEAEDVGVYFCSQSTH
VPYTFGGGTKLEIK

SEQ ID No. 33
DIVMTQSPLSLPVTPGEPASISCRSSQRLVHSNGNTYLHWYLQKPGQSP
RLLIYRVSNRFPGVPDRFSGSGSGTDFTLKISRVEAEDVGVYFCSQSTH
VPYTFGQGTKLEIK
```

-continued

SEQ ID No. 34
DIVMTQSPLSLPVTPGEPASISC<u>RSSQRLVHSNGNTYLH</u>WYLQKPGQSP
RLLIY<u>RVSNRFP</u>GVPDRFSGSGSGTDFTLKISRVEAEDVGVYYC<u>SQSTH
VPYT</u>FGGGTKLEIK

The anti-TRBC1 antigen binding domain may comprise:
a) a VH domain which comprises JOVI-1 VH CDRs with the human framework H-AF062256 or a variant thereof; and
b)) a VH domain which comprises JOVI-1 VL CDRs with the human framework 3aaz or a variant thereof.

The variant may have 5 or fewer, 4 or fewer, 3 or fewer, 2 or 1 mutation compared to the wild-type human framework region sequence.

The VH domain may comprise the sequence shown as SEQ ID No. 9, SEQ ID No. 12, SEQ ID No. 13, SEQ ID No. 14, SEQ ID No. 15, SEQ ID No. 16, SEQ ID No. 17 or SEQ ID No. 18. The VL domain may comprise the sequence shown as SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34

The anti-TRBC1 antigen binding domain may comprise:
a) a VH domain which comprises the sequence shown as SEQ ID No 9; and
b)) a VH domain which comprises the sequence shown as SEQ ID No. 19.

Antibody

The antigen-binding domain of the first aspect of the invention may be an antibody or a functional fragment thereof. The antibody may be a therapeutic antibody, such as a depleting antibody. The antibody may be a bispecific antibody which binds TRBC1 together with another antigen. The antibody may, for example, be a dual affinity re-targeting antibody.

The term 'depleting antibody' is used in the conventional sense to relate to an antibody which binds to an antigen (i.e. TRBC1) present on a target T-cell and mediates death of the target T-cell. The administration of a depleting antibody to a subject therefore results in a reduction/decrease in the number of cells within the subject which express the target antigen.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'2, Fv, single chain Fv (ScFv) fragment, and scFv-Fc fusion or diabody, triabody or nanobody which retains the antigen specificity of the full antibody. The antibody may be a bifunctional antibody. The antibody may be non-human, chimeric, humanised or fully human.

Conjugates

The antibody may be a conjugate of the antibody and another agent or antibody, for example the conjugate may be a detectable entity or a chemotherapeutic entity.

The detectable entity may be a fluorescent moiety, for example a fluorescent peptide. A "fluorescent peptide" refers to a polypeptide which, following excitation, emits light at a detectable wavelength. Examples of fluorescent proteins include, but are not limited to, fluorescein isothiocyanate (FITC), phycoerythrin (PE), allophycocyanin (APC), green fluorescent protein (GFP), enhanced GFP, red fluorescent protein (RFP), blue fluorescent protein (BFP) and mCherry.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinum coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate;

estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

A TRBC1-specific antibody-drug conjugate enables the targeted delivery of a chemotherapeutic entity to cells which express TRBC1.

Bi-Specific T-Cell Engagers

A wide variety of molecules have been developed which are based on the basic concept of having two antibody-like binding domains.

Bispecific T-cell engaging molecules are a class of bispecific antibody-type molecules that have been developed, primarily for the use as anti-cancer drugs. They direct a host's immune system, more specifically the T cells' cytotoxic activity, against a target cell, such as a cancer cell. In these molecules, one binding domain binds to a T cell via the CD3 receptor, and the other to a target cells such as a tumor cell (via a tumor specific molecule). Since the bispecific molecule binds both the target cell and the T cell, it brings the target cell into proximity with the T cell, so that the T cell can exert its effect, for example, a cytotoxic effect on a cancer cell. The formation of the T cell:bispecific Ab:cancer cell complex induces signaling in the T cell leading to, for example, the release of cytotoxic mediators. Ideally, the agent only induces the desired signaling in the presence of the target cell, leading to selective killing.

Bispecific T-cell engaging molecules have been developed in a number of different formats, but one of the most common is a fusion consisting of two single-chain variable fragments (scFvs) of different antibodies. These are sometimes known as BiTEs (Bi-specific T-cell Engagers).

The present invention therefore provides a bi-specific molecule which selectively recognises TRBC1 and is capable of activating a T cell. For example the agent may be a BiTE. The agent may comprise:
(i) a first domain which binds TRBC1, having an antigen-binding domain as defined above; and
(ii) a second domain capable of activating a T cell.

The bi-specific molecule may comprise a signal peptide to aid in its production. The signal peptide may cause the bi-specific molecule to be secreted by a host cell, such that the bi-specific molecule can be harvested from the host cell supernatant.

The signal peptide may be at the amino terminus of the molecule. The bi-specific molecule may have the general formula: Signal peptide—first domain—second domain.

The bi-specific molecule may comprise a spacer sequence to connect the first domain with the second domain and spatially separate the two domains.

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

Chimeric Antigen Receptor (CAR)

The present invention provides a CAR which selectively recognises TRBC1.

Chimeric antigen receptors (CARs), also known as chimeric T-cell receptors, artificial T-cell receptors and chimeric immunoreceptors, are engineered receptors, which graft an arbitrary specificity onto an immune effector cell. In a classical CAR, the specificity of a monoclonal antibody is grafted on to a T-cell. CAR-encoding nucleic acids may be transferred to T-cells using, for example, retroviral vectors. In this way, a large number of cancer-specific T-cells can be generated for adoptive cell transfer. Phase I clinical studies of this approach show efficacy.

The target-antigen binding domain of a CAR is commonly fused via a spacer and transmembrane domain to an endodomain, which comprises or associates with an intercellular T-cell signalling domain. When the CAR binds the target-antigen, this results in the transmission of an activating signal to the T-cell it is expressed on.

The CAR may also comprise a transmembrane domain which spans the membrane. It may comprise a hydrophobic alpha helix. The transmembrane domain may be derived from CD28, which gives good receptor stability.

The endodomain is the portion of the CAR involved in signal-transmission. The endodomain either comprises or associates with an intracellular T-cell signalling domain. After antigen recognition, receptors cluster and a signal is transmitted to the cell. The most commonly used T-cell signalling component is that of CD3-zeta which contains 3 ITAMs. This transmits an activation signal to the T-cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of the CAR may comprise the CD28 endodomain and OX40 and CD3-Zeta endodomain.

Alternatively, the CAR of the second aspect of the invention may lack an intracellular signalling domain, but may be capable of associating with a separate molecule which provides the signalling functionality.

CAR signalling systems have previously been described which comprise two parts: a CAR, which comprises the antigen binding domain and a transmembrane domain; and an intracellular signalling component which comprises an intracellular signalling domain. One or more co-stimulatory domains may be located on the CAR and/or the intracellular signalling component.

Heterodimerisation between the CAR and the intracellular signalling component produces a functional CAR system. Heterodimerisation may occur spontaneously, as described in WO2016/124930; or it may occur only in the presence of a chemical inducer of dimerization (CID), as described in WO2015/150771. In a third alternative, heterodimerization is disrupted by the presence of an agent, such as a particular small molecule, so CAR-mediated signalling only occurs in the absence of the agent. Such a system is described in WO2016/030691.

The CAR may comprise a signal peptide so that when the CAR is expressed inside a cell, such as a T-cell, the nascent protein is directed to the endoplasmic reticulum and subsequently to the cell surface, where it is expressed.

The CAR may comprise a spacer sequence to connect the TRBC-binding domain with the transmembrane domain and spatially separate the TRBC-binding domain from the membrane. A flexible spacer allows to the TRBC-binding domain to orient in different directions to enable TRBC binding.

The spacer sequence may, for example, comprise an IgG1 Fc region, an IgG1 hinge or a CD8 stalk, or a combination thereof.

Nucleic Acid

The present invention further provides a nucleic acid encoding a BiTE or CAR as defined above.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The present invention also provides a nucleic acid construct which comprises a first nucleic acid encoding a CAR as defined above; and a second nucleic acid encoding a suicide gene.

Suitable suicide genes for use in a CAR-expressing cell of the invention include RQR8, which is described in WO2013/153391; and RapCasp9, which is described in WO2016/135470.

In the nucleic acid construct described above, the first and second nucleic acid sequences may be in either order.

Vector

The present invention also provides a vector, or kit of vectors, which comprises one or more nucleic acid sequence(s) or nucleic acid construct(s) of the invention. Such a vector may be used to introduce the nucleic acid sequence(s) or construct(s) into a host cell, for example, so that it expresses a CAR having an antigen-binding domain according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention also relates to a cell, such as an immune cell, comprising a CAR according to the first aspect of the invention.

The cell may comprise a nucleic acid, a nucleic acid construct or a vector of the present invention.

The cell may be a T-cell or a natural killer (NK) cell.

T cell may be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing the a CAR according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing a CAR according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR cells are generated by introducing DNA or RNA coding for the CAR by one of many means including transduction with a viral vector, transfection with DNA or RNA.

The CAR-expressing cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding a CAR according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with a nucleic acid sequence(s) encoding a CAR of the invention.

The T or NK cells may then by purified, for example, selected on the basis of expression of the antigen-binding domain of the antigen-binding polypeptide.

The present invention also provides a kit which comprises a T or NK cell comprising a CAR according to the first aspect of the invention.

Pharmaceutical Composition

The present invention also relates to a pharmaceutical composition containing a therapeutic entity such as a CAR-expressing cell, a therapeutic antibody or conjugate thereof, or a bi-specific T-cell engager of the present invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

T-Cell Lymphoma and/or Leukaemia

The present invention relates to agents, cells and methods for treating a T-cell lymphoma and/or leukaemia.

A method for treating a T-cell lymphoma and/or leukaemia relates to the therapeutic use of an agent. Herein the agent may be administered to a subject having an existing disease of T-cell lymphoma and/or leukaemia in order to lessen, reduce or improve at least one symptom associated with the disease and/or to slow down, reduce or block the progression of the disease.

The method of the present invention may be used for the treatment of any lymphoma and/or leukaemia associated with the clonal expansion of a cell expressing a T-cell receptor (TCR) comprising TRBC1.

The method of the present invention may be used to treat a T-cell lymphoma in which the malignant T-cell expresses a TCR comprising TRBC1. 'Lymphoma' is used herein according to its standard meaning to refer to a cancer which typically develops in the lymph nodes, but may also affect the spleen, bone marrow, blood and other organs. Lymphoma typically presents as a solid tumour of lymphoid cells. The primary symptom associated with lymphoma is lymphadenopathy, although secondary (B) symptoms can include fever, night sweats, weight loss, loss of appetite, fatigue, respiratory distress and itching.

The method of the present invention may be used to treat a T-cell leukaemia in which the malignant T-cell expresses a TCR comprising TRBC1. 'Leukaemia' is used herein according to its standard meaning to refer to a cancer of the blood or bone marrow.

The following is an illustrative, non-exhaustive list of diseases which may be treated by the method of the present invention.

Peripheral T-Cell Lymphoma

Peripheral T-cell lymphomas are relatively uncommon lymphomas and account fewer than 10% of all non-Hodgkin lymphomas (NHL). However, they are associated with an aggressive clinical course and the causes and precise cellular origins of most T-cell lymphomas are still not well defined.

Lymphoma usually first presents as swelling in the neck, underarm or groin. Additional swelling may occur where other lymph nodes are located such as in the spleen. In general, enlarged lymph nodes can encroach on the space of blood vessels, nerves, or the stomach, leading to swollen arms and legs, to tingling and numbness, or to feelings of being full, respectively. Lymphoma symptoms also include nonspecific symptoms such as fever, chills, unexplained weight loss, night sweats, lethargy, and itching.

The WHO classification utilizes morphologic and immunophenotypic features in conjunction with clinical aspects and in some instances genetics to delineate a prognostically and therapeutically meaningful categorization for peripheral T-cell lymphomas (Swerdlow et al.; WHO classification of tumours of haematopoietic and lymphoid tissues. 4th ed.; Lyon: IARC Press; 2008). The anatomic localization of neoplastic T-cells parallels in part their proposed normal cellular counterparts and functions and as such T-cell lymphomas are associated with lymph nodes and peripheral blood. This approach allows for better understanding of some of the manifestations of the T-cell lymphomas, including their cellular distribution, some aspects of morphology and even associated clinical findings.

The most common of the T-cell lymphomas is peripheral T-cell lymphoma, not otherwise specified (PTCL-NOS) comprising 25% overall, followed by angioimmunoblastic T-cell lymphoma (AITL) (18.5%)

Peripheral T-Cell Lymphoma, Not Otherwise Specified (PTCL-NOS)

PTCL-NOS comprises over 25% of all peripheral T-cell lymphomas and NK/T-cell lymphomas and is the most common subtype. It is determined by a diagnosis of exclusion, not corresponding to any of the specific mature T-cell lymphoma entities listed in the current WHO 2008. As such it is analogous to diffuse large B-cell lymphoma, not otherwise specified (DLBCL-NOS).

Most patients are adults with a median age of 60 and a male to female ratio 2:1. The majority of cases are nodal in origin, however, extranodal presentations occur in approximately 13% of patients and most commonly involve skin and gastrointestinal tract.

The cytologic spectrum is very broad, ranging from polymorphous to monomorphous. Three morphologically defined variants have been described, including lymphoepithelioid (Lennert) variant, T-zone variant and follicular variant. The lymphoepithelioid variant of PTCL contains abundant background epithelioid histiocytes and is commonly positive for CD8. It has been associated with a better prognosis. The follicular variant of PTCL-NOS is emerging as a potentially distinct clinicopathologic entity.

The majority of PTCL-NOS have a mature T-cell phenotype and most cases are CD4-positive. 75% of cases show variable loss of at least one pan T-cell marker (CD3, CD2, CD5 or CD7), with CD7 and CD5 being most often downregulated. CD30 and rarely CD15 can be expressed, with CD15 being an adverse prognostic feature. CD56 expression, although uncommon, also has negative prognostic impact. Additional adverse pathologic prognostic factors include a proliferation rate greater than 25% based on KI-67 expression, and presence of more than 70% transformed cells. Immunophenotypic analysis of these lymphomas has offered little insight into theft biology.

Angioimmunoblastic T-Cell Lymphoma (AITL)

AITL is a systemic disease characterized by a polymorphous infiltrate involving lymph nodes, prominent high endothelial venules (HEV) and peri-vascular expansion of follicular dendritic cell (FDC) meshworks. AITL is considered as a de-novo T-cell lymphoma derived from $\alpha\beta$ T-cells of follicular helper type (TFH), normally found in the germinal centres.

AITL is the second most common entity among peripheral T-cell lymphoma and NK/T-cell lymphomas, comprising about 18.5% of cases. It occurs in middle aged to elderly adults, with a median age of 65 years old, and an approximately equal incidence in males and females. Clinically, patients usually have advanced stage disease, with generalized lymphadenopathy, hepatosplenomegaly and prominent constitutional symptoms. Skin rash with associated pruritus is commonly present. There is often polyclonal hypergammaglobulinemia, associated with autoimmune phenomena.

Three different morphologic patterns are described in AITL. The early lesion of AITL (Pattern I) usually shows preserved architecture with characteristic hyperplastic follicles. The neoplastic proliferation is localized to the periphery of the follicles. In Pattern II the nodal architecture is partially effaced with retention of few regressed follicles. The subcapsular sinuses are preserved and even dilated. The paracortex contains arborizing HEV and there is a proliferation of FDC beyond the B-cell follicle. The neoplastic cells are small to medium in size, with minimal cytologic atypia. They often have clear to pale cytoplasm, and may show distinct T-cell membranes. A polymorphous inflammatory background is usually evident.

Although AITL is a T-cell malignancy, there is a characteristic expansion of B-cells and plasma cells, which likely reflects the function of the neoplastic cells as TFH cells. Both EBV-positive and EBV-negative B-cells are present. Occasionally, the atypical B-cells may resemble Hodgkin/

Reed-Sternberg-like cells morphologically and immunophenotypically, sometimes leading to a diagnostic confusion with that entity. The B-cell proliferation in AITL may be extensive and some patients develop secondary EBV-positive diffuse large B-cell lymphomas (DLBCL) or—more rarely—EBV-negative B-cell tumors, often with plasmacytic differentiation.

The neoplastic CD4-positive T-cells of AITL show strong expression of CD10 and CD279 (PD-1) and are positive for CXCL13. CXCL13 leads to an increased B-cell recruitment to lymph nodes via adherence to the HEV, B-cell activation, plasmacytic differentiation and expansion of the FDC meshworks, all contributing to the morphologic and clinical features of AITL. Intense PD-1-expression in the perifollicular tumor cells is particularly helpful in distinguishing AITL Pattern I from reactive follicular and paracortical hyperplasia.

The follicular variant of PTCL-NOS is another entity with a TFH phenotype. In contradistinction to AITL, it does not have prominent HEV or extra-follicular expansion of FDC meshworks. The neoplastic cells may form intrafollicular aggregates, mimicking B-cell follicular lymphoma, but also can have interfollicular growth pattern or involve expanded mantle zones. Clinically, the follicular variant of PTCL-NOS is distinct from AITL as patients more often present with early stage disease with partial lymph node involvement and may lack the constitutional symptoms associated with AITL.

Anaplastic Large Cell Lymphoma (ALCL)

ALCL may be subdivided as ALCL-'anaplastic lymphoma kinase' (ALK)+ or ALCL-ALK−.

ALCL-ALK+ is one of the best-defined entities within the peripheral T-cell lymphomas, with characteristic "hallmark cells" bearing horseshoe-shaped nuclei and expressing ALK and CD30. It accounts for about 7% of all peripheral T-cell and NK-cell lymphomas and is most common in the first three decades of life. Patients often present with lymphadenopathy, but the involvement of extranodal sites (skin, bone, soft tissues, lung, liver) and B symptoms is common.

ALCL, ALK+ shows a wide morphologic spectrum, with 5 different patterns described, but all variants contain some hallmark cells. Hallmark cells have eccentric horseshoe- or kidney-shaped nuclei, and a prominent perinuclear eosinophilic Golgi region. The tumour cells grow in a cohesive pattern with predilection for sinus involvement. Smaller tumour cells predominate in the small cell variant, and in the lymphohistiocytic variant abundant histiocytes mask the presence of tumour cells, many of which are small.

By definition, all cases show ALK and CD30 positivity, with expression usually weaker in the smaller tumour cells. There is often loss of pan-T-cell markers, with 75% of cases lacking surface expression of CD3.

ALK expression is a result of a characteristic recurrent genetic alteration consisting of a rearrangement of ALK gene on chromosome 2p23 to one of the many partner genes, resulting in an expression of chimeric protein. The most common partner gene, occurring in 75% of cases, is Nucleophosmin (NPM1) on chromosome 5q35, resulting in t(2;5)(p23;q35). The cellular distribution of ALK in different translocation variants may vary depending on the partner gene.

ALCL-ALK− is included as a provisional category in the 2008 WHO classification. It is defined as a CD30 positive T-cell lymphoma that is morphologically indistinguishable from ALCL-ALK+ with a cohesive growth pattern and presence of hallmark cells, but lacking ALK protein expression.

Patients are usually adults between the ages of 40 and 65, in contrast to ALCL-ALK+, which is more common in children and young adults. ALCL-ALK− can involve both lymph nodes and extranodal tissues, although the latter is seen less commonly than in ALCL-ALK+. Most cases of ALCL-ALK− demonstrate effacement of lymph node architecture by sheets of cohesive neoplastic cells with typical "hallmark" features. In contrast to the ALCL-ALK+, the small cell morphologic variant is not recognized.

Unlike its ALK+ counterpart, ALCL-ALK− shows a greater preservation of surface T-cell marker expression, while the expression of cytotoxic markers and epithelial membrane antigen (EMA) is less likely. Gene expression signatures and recurrent chromosomal imbalances are different in ALCL-ALK− and ALCL-ALK+, confirming that they are distinct entities at a molecular and genetic level.

ALCL-ALK− is clinically distinct from both ALCL-ALK+ and PTCL-NOS, with significant differences in prognosis among these three different entities. The 5 year overall survival of ALCL-ALK− is reported as 49% which is not as good as that of ALCL-ALK+ (at 70%), but at the same time it is significantly better than that of PTCL-NOS (32%).

Enteropathy-Associated T-Cell Lymphoma (EATL)

EATL is an aggressive neoplasm which thought to be derived from the intraepithelial T-cells of the intestine. Two morphologically, immunohistochernically and genetically distinct types of EATL are recognized in the 2008 WHO classification: Type I (representing the majority of EATL) and Type II (comprising 10-20% of cases).

Type I EATL is usually associated with overt or clinically silent gluten-sensitive enteropathy, and is more often seen in patients of Northern European extraction due to high prevalence of celiac disease in this population.

Most commonly, the lesions of EATL are found in the jejunum or ileum (90% of cases), with rare presentations in duodenum, colon, stomach, or areas outside of the gastrointestinal tract. The intestinal lesions are usually multifocal with mucosal ulceration. Clinical course of EATL is aggressive with most patients dying of disease or complications of disease within 1 year.

The cytological spectrum of EATL type I is broad, and some cases may contain anaplastic cells. There is a polymorphous inflammatory background, which may obscure the neoplastic component in some cases. The intestinal mucosa in regions adjacent to the tumour often shows features of celiac disease with blunting of the villi and increased numbers of intraepithelial lymphocytes (IEL), which may represent lesional precursor cells.

By immunohistochemistry, the neoplastic cells are often CD3+CD4−CD8−CD7+CD5−CD56−βF1+, and contain cytotoxic granule-associated proteins (TIA-1, granzyme B, perforin). CD30 is partially expressed in almost all cases. CD103, which is a mucosal homing receptor, can be expressed in EATL.

Type II EATL, also referred to as monomorphic CD56+ intestinal T-cell lymphoma, is defined as an intestinal tumour composed of small- to medium-sized monomorphic T-cells that express both CD8 and CD56. There is often a lateral spread of tumour within the mucosa, and absence of an inflammatory background. The majority of cases express the γδ TCR, however there are cases associated with the αβ TCR.

Type II EATL has a more world-wide distribution than Type I EATL and is often seen in Asians or Hispanic populations, in whom celiac disease is rare. In individuals of European descent EATL, II represents about 20% of intestinal T-cell lymphomas, with a history of celiac disease in at least a subset of cases. The clinical course is aggressive.

Hepatosplenic T-Cell Lymphoma (HSTL)

HSTL is an aggressive systemic neoplasm generally derived from γδ cytotoxic T-cells of the innate immune system, however, it may also be derived from αβ T-cells in rare cases. It is one of the rarest T-cell lymphomas, and typically affects adolescents and young adults (median age, 35 years) with a strong male predominance.

Extranodal NK/T-Cell Lymphoma Nasal Type

Extranodal NK/T-cell lymphoma, nasal type, is an aggressive disease, often with destructive midline lesions and necrosis. Most cases are of NK-cell derivation, but some cases are derived from cytotoxic T-cells. It is universally associated with Epstein-Barr Virus (EBV).

Cutaneous T-Cell Lymphoma

The method of the present invention may also be used to treat cutaneous T-cell lymphoma.

Cutaneous T-cell lymphoma (CTCL) is characterised by migration of malignant T-cells to the skin, which causes various lesions to appear. These lesions change shape as the disease progresses, typically beginning as what appears to be a rash and eventually forming plaques and tumours before metastasizing to other parts of the body.

Cutaneous T-cell lymphomas include those mentioned in the following illustrative, non-exhaustive list; mycosis fungoides, pagetoid reticulosis, Sézary syndrome, granulomatous slack skin, lymphomatoid papulosis, pityriasis lichenoides chronica, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma and angiocentric lymphoma.

The signs and symptoms of CTCL vary depending on the specific disease, of which the two most common types are mycosis fungoides and Sézary syndrome. Classic mycosis fungoides is divided into three stages:

Patch (atrophic or nonatrophic): Nonspecific dermatitis, patches on lower trunk and buttocks; minimal/absent pruritus;

Plaque: Intensely pruritic plaques, lymphadenopathy; and

Tumor: Prone to ulceration

Sézary syndrome is defined by erythroderma and leukemia. Signs and symptoms include edematous skin, lymphadenopathy, palmar and/or plantar hyperkeratosis, alopecia, nail dystrophy, ectropion and hepatosplenomegaly.

Of all primary cutaneous lymphomas, 65% are of the T-cell type. The most common immunophenotype is CD4 positive. There is no common pathophysiology for these diseases, as the term cutaneous T-cell lymphoma encompasses a wide variety of disorders.

The primary etiologic mechanisms for the development of cutaneous T-cell lymphoma (ie, mycosis fungoides) have not been elucidated. Mycosis fungoides may be preceded by a T-cell-mediated chronic inflammatory skin disease, which may occasionally progress to a fatal lymphoma.

Primary Cutaneous ALCL (C-ALCL)

C-ALCL is often indistinguishable from ALC-ALK− by morphology. It is defined as a cutaneous tumour of large cells with anaplastic, pleomorphic or immunoblastic morphology with more than 75% of cells expressing CD30. Together with lymphomatoid papulosis (LyP), C-ALCL belongs to the spectrum of primary cutaneous CD30-positive T-cell lymphoproliferative disorders, which as a group comprise the second most common group of cutaneous T-cell lymphoproliferations after mycosis fungoides.

The immunohistochemical staining profile is quite similar to ALCL-ALK−, with a greater proportion of cases staining positive for cytotoxic markers. At least 75% of the tumour cells should be positive for CD30. CD15 may also be expressed, and when lymph node involvement occurs, the differential with classical Hodgkin lymphoma can be difficult. Rare cases of ALCL-ALK+ may present with localized cutaneous lesions, and may resemble C-ALCL.

T-Cell Acute Lymphoblastic Leukaemia

T-cell acute lymphoblastic leukaemia (T-ALL) accounts for about 15% and 25% of ALL in paediatric and adult cohorts respectively. Patients usually have high white blood cell counts and may present with organomegaly, particularly mediastinal enlargement and CNS involvement.

The method of the present invention may be used to treat T-ALL which is associated with a malignant T cell which expresses a TCR comprising TRBC1.

T-Cell Prolymphocytic Leukaemia

T-cell-prolymphocytic leukemia (T-PLL) is a mature T-cell leukaemia with aggressive behaviour and predilection for blood, bone marrow, lymph nodes, liver, spleen, and skin involvement. T-PLL primarily affects adults over the age of 30. Other names include T-cell chronic lymphocytic leukaemia, "knobby" type of T-cell leukaemia, and T-prolymphocytic leukaemia/T-cell lymphocytic leukaemia.

In the peripheral blood, T-PLL consists of medium-sized lymphocytes with single nucleoli and basophilic cytoplasm with occasional blebs or projections. The nuclei are usually round to oval in shape, with occasional patients having cells with a more irregular nuclear outline that is similar to the cerebriform nuclear shape seen in Sézary syndrome. A small cell variant comprises 20% of all T-PLL cases, and the Sézary cell-like (cerebriform) variant is seen in 5% of cases.

T-PLL has the immunophenotype of a mature (post-thymic) T-lymphocyte, and the neoplastic cells are typically positive for pan-T antigens CD2, CD3, and CD7 and negative for TdT and CD1a. The immunophenotype CD4+/CD8− is present in 60% of cases, the CD4+/CD8+ immunophenotype is present in 25%, and the CD4−/CD8+ immunophenotype is present in 15% of cases Pharmaceutical Composition The method of the present invention may comprise the step of administering the agent in the form of a pharmaceutical composition.

The agent may be administered with a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents.

Administration

The administration of the agent can be accomplished using any of a variety of routes that make the active ingredient bioavailable. For example, the agent can be administered by oral and parenteral routes, intraperitoneally, intravenously, subcutaneously, transcutaneously, intramuscularly, via local delivery for example by catheter or stent.

Typically, a physician will determine the actual dosage which will be most suitable for an individual subject and it will vary with the age, weight and response of the particular patient. The dosage is such that it is sufficient to reduce or deplete the number of clonal T-cells expressing TRBC1.

The invention will now be further described by way of Examples, which are meant to serve to assist one of ordinary skill in the art in carrying out the invention and are not intended in any way to limit the scope of the invention.

EXAMPLES

Example 1—Heavy and Light Chain Graft Selection

Humanised VH domains were constructed with the JOVI-1 VH CDRs following human VH frameworks: H-AF062256, H-EF177999, H-KF688165. Humanised VL domains were constructed with the 3aaz human framework.

Antibodies were created with either a humanised VH domain and the murine JOVI-1 VL domain; the murine VH domain and a humanised VL domain; or a humanised VH domain and a humanised VL domain (see FIG. 4).

Binding to TRBC1 was tested by ELISA and the results are shown in FIG. 5.

All of the chimeric and humanised binder combinations were found to be capable of binding TRBC1 and binding was similar to the chimeric antibody having murine VH and VL domains.

Example 2—Making and Testing Back Mutated Constructs

A series of back-mutated binders for human framework H-AF062256 were created, as shown in Table 1, in which back mutations are shown in bold.

TABLE 1

| Construct | Heavy Chain | Heavy chain Mutations |
|---|---|---|
| Jovi Hum 8 | H-AF 1 | Q3, V20, M48, R71, T73 |
| Jovi Hum 16 | H-AF 2 | Q3, V20, M48, R71, K73 |
| Jovi Hum 17 | H-AF 3 | Q3, V20, M48, S71, T73 |
| Jovi Hum 18 | H-AF 4 | Q3, V20, M48, S71, K73 |
| Jovi Hum 19 | H-AF 5 | Q3, V20, I48, R71, T73 |
| Jovi Hum 20 | H-AF 6 | Q3, V20, I48, R71, K73 |
| Jovi Hum 21 | H-AF 7 | Q3, V20, I48, S71, T73 |
| Jovi Hum 22 | H-AF 8 | Q3, V20, I48, S71, K73 |
| Jovi Hum 23 | H-AF 9 | Q3, M20, M48, R71, T73 |
| Jovi Hum 24 | H-AF 10 | Q3, M20, M48, R71, K73 |
| Jovi Hum 25 | H-AF 11 | Q3, M20, M48, S71, T73 |
| Jovi Hum 26 | H-AF 12 | Q3, M20, M48, S71, K73 |
| Jovi Hum 27 | H-AF 13 | Q3, M20, I48, R71, T73 |
| Jovi Hum 28 | H-AF 14 | Q3, M20, I48, R71, K73 |
| Jovi Hum 29 | H-AF 15 | Q3, M20, I48, S71, T73 |
| Jovi Hum 30 | H-AF 16 | Q3,M20, I48, S71, K73 |
| Jovi Hum 31 | H-AF 17 | R3, V20, M48, R71, T73 |
| Jovi Hum 32 | H-AF 18 | R3, V20, M48, R71, K73 |
| Jovi Hum 33 | H-AF 19 | R3, V20, M48, S71, T73 |
| Jovi Hum 34 | H-AF 20 | R3, V20, M48, S71, K73 |
| Jovi Hum 35 | H-AF 21 | R3, V20, I48, R71, T73 |
| Jovi Hum 36 | H-AF 22 | R3, V20, I48, R71,K73 |
| Jovi Hum 37 | H-AF 23 | R3, V20, I48, S71, T73 |
| Jovi Hum 38 | H-AF 24 | R3, V20, I48, S71, K73 |
| Jovi Hum 39 | H-AF 25 | R3, M20, M48, R71, T73 |
| Jovi Hum 40 | H-AF 26 | R3, M20, M48, R71,K73 |
| Jovi Hum 41 | H-AF 27 | R3, M20, M48, S71, T73 |
| Jovi Hum 42 | H-AF 28 | R3, M20, M48, S71, K73 |
| Jovi Hum 43 | H-AF 29 | R3, M20, I48, R71, T73 |
| Jovi Hum 44 | H-AF 30 | R3, M20, I48, R71, K73 |
| Jovi Hum 45 | H-AF 31 | R3, M20, I48, S71, T73 |
| Jovi Hum 46 | H-AF 32 | R3, M20, I48, S71, K73 |

The binders had a humanised VL domain comprising the 3aaz framework.

Figure 6:
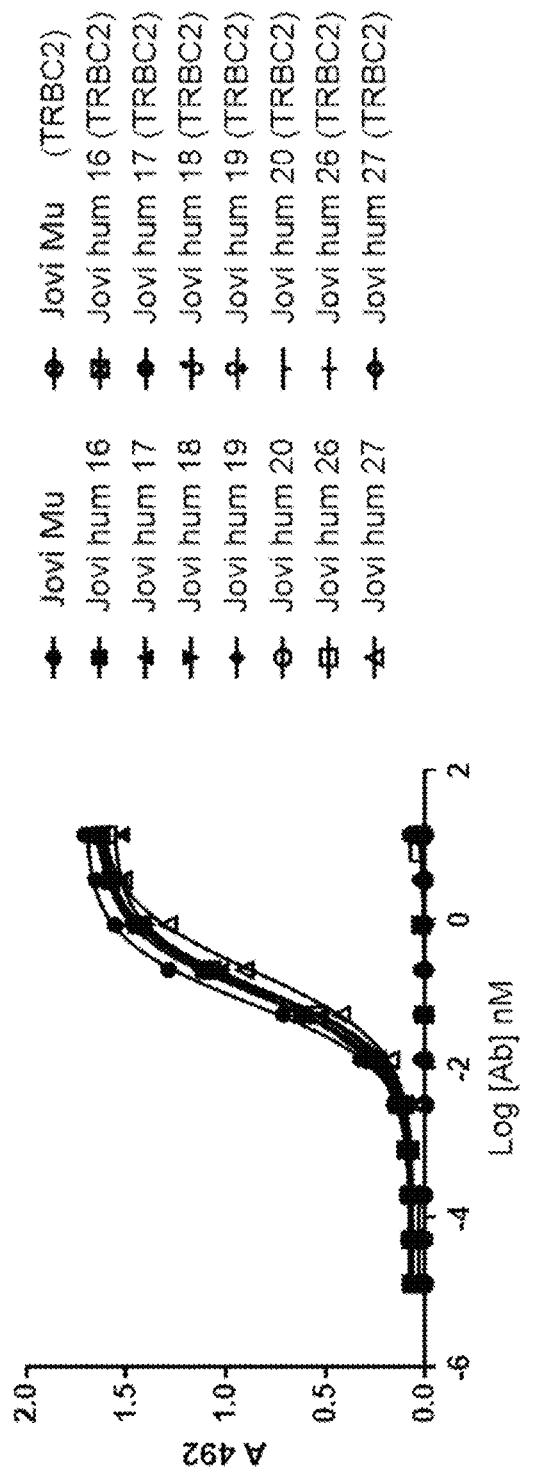
FIG. 6: TRBC1/TRBC2 binding of back-mutated constructs. A series of back-mutated VH constructs were created based on the H-AF062256 framework as shown in Table 1. These VH domains were used to create humanized antibodies in combination with a VL domain having the 3aaz human framework. The antibodies were tested for binding to TRBC1 and TRBC2 by ELISA.

Binding to TRBC1 and TRBC2 was tested by ELISA and the results are shown in FIG. 6. All the constructs bound TRBC1 but not TRBC2 and displayed a similar EC50 to the chimeric antibody having murine VH and VL domains (Jovi-Mu). This shows that following CDR grafting, the specificity and affinity of the murine antibody is retained in the humanised antibodies.

Example 3—Investigating the Stability of Humanised mAbs and scFvs

The stability of the binders described in Example 2 was tested by differential scanning fluorimetry. Proteins were stored in PBS at 150 ug/ml prior to addition of sypro orange dye at a protein:dye ratio of 5000:1. Solutions were mixed and placed in a qPCR machine and run in FRET mode. Solutions were held at 15° C. for 10 min followed by a temperature ramp to 95° C. with 0.5° C. increments and a 30 sec hold at each step. A fluorescence readout was obtained after each step. To obtain the Tm value (Equilibrium constant; Unfolded protein=Folded protein) the first derivative of the change in fluorescence ($\Delta RFU/\Delta° C.$) was plot against the change in temperature ($\Delta° C.$).

Figure 7:
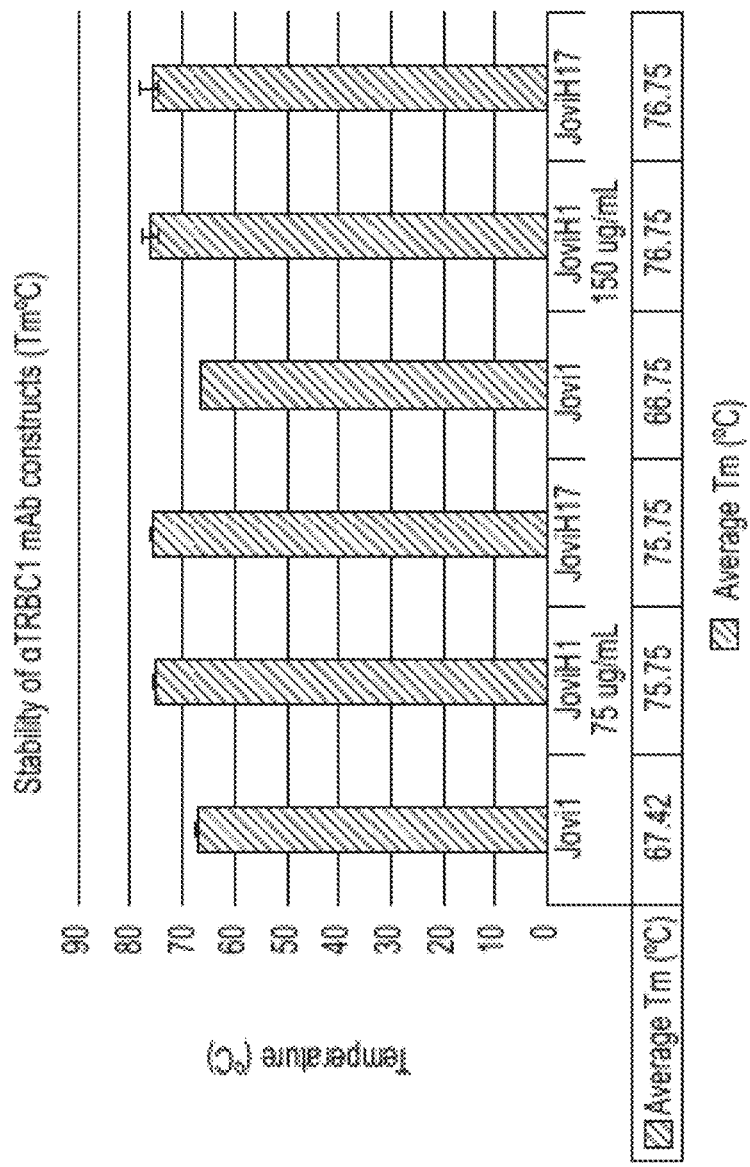
FIG. 7: Stability of anti-TRBC1 antibody constructs (Tm° C.). Stability of antibodies comprising the back-mutated constructs shown in Table 1 with a 3aaz humanised light chain compared with the murine JOVI-1 antibody.

The results are shown in FIG. 7. It was found that usage of the human framework increases stability of the binder in a mAb formats.

A similar experiment was conducted to investigate the stability of the equivalent binders in an scFv format. For this study, differential scanning colourimetry was used. Experiments were performed using a CAP DSC system. Proteins in storage buffer (1×PBS) were placed in the calorimeter sample cell and the reference cell filled with the storage buffer alone. The cells were stabilized inside the calorimeter for 1 h at 25° C. before heating up to the final temperature of 100° C. at a rate of 200° C. per hour. The denaturation temperature, Tm, corresponding to the maximum of the transition peak, was determined from at least two replicate runs and varied not more than 0.25° C.

Figure 8:
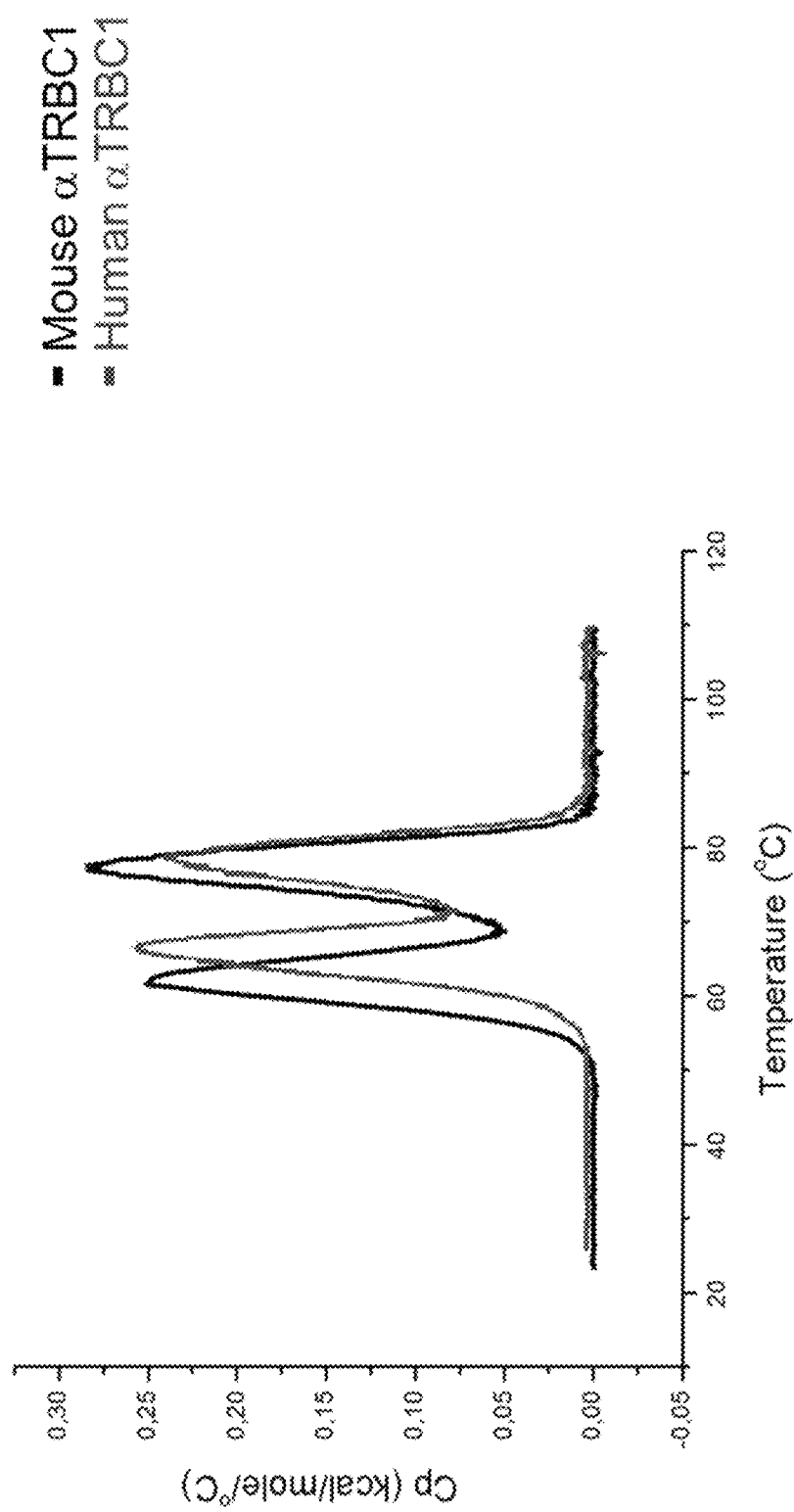
FIG. 8: Stability of anti-TRBC1 antibody constructs (Tm° C.).

The results for one binder scFv comparison are shown in FIG. 8. The melting temperature of the mouse Jovi-1 scFv was 61° C., whereas the melting temperature for humanised scFv (H-AF1, 3aaz) was 65° C.

Figure 9:
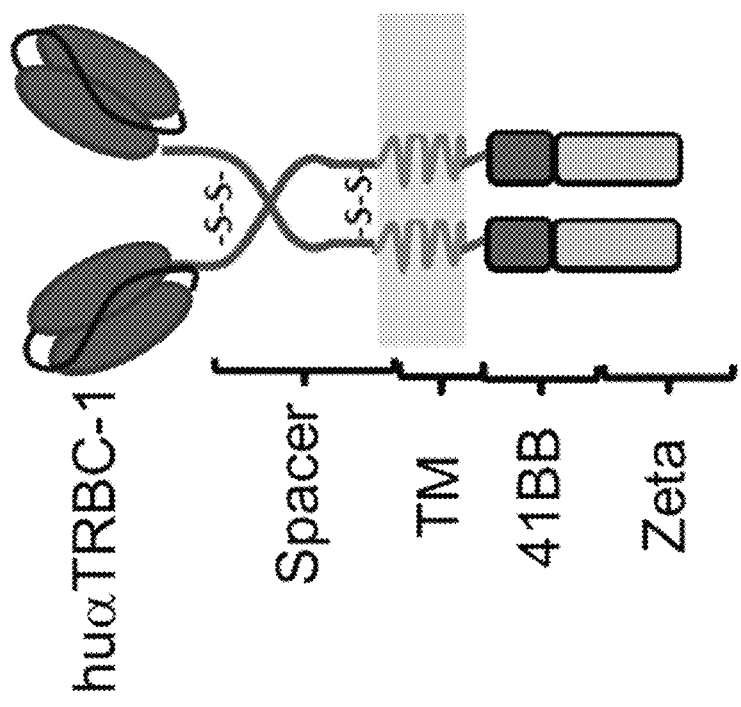
FIG. 9: Schematic diagram illustrating a humanised anti-TRBC1 chimeric antigen receptor (CAR)

Example 4—Generation of a Chimeric Antigen Receptor (CAR) With a Humanised Anti-TRBC1 Antigen Binding Domain A second generation CAR was designed having a 41BB and CD3 zeta endodomain and an antigen binding domain comprising a humanised JOVI-1 scFv (H-AF1, 3aaz) as illustrated schematically in FIG. 9. Primary human T-cells from normal donors were transduced with retroviral vectors expressing the anti-TRBC1 CAR or an irrelevant EGFRvIII CAR as a negative control. The capacity of the cells to kill either TRBC1- or TRBC2-expressing target cells was investigated using flow cytometry.

Figure 10A:
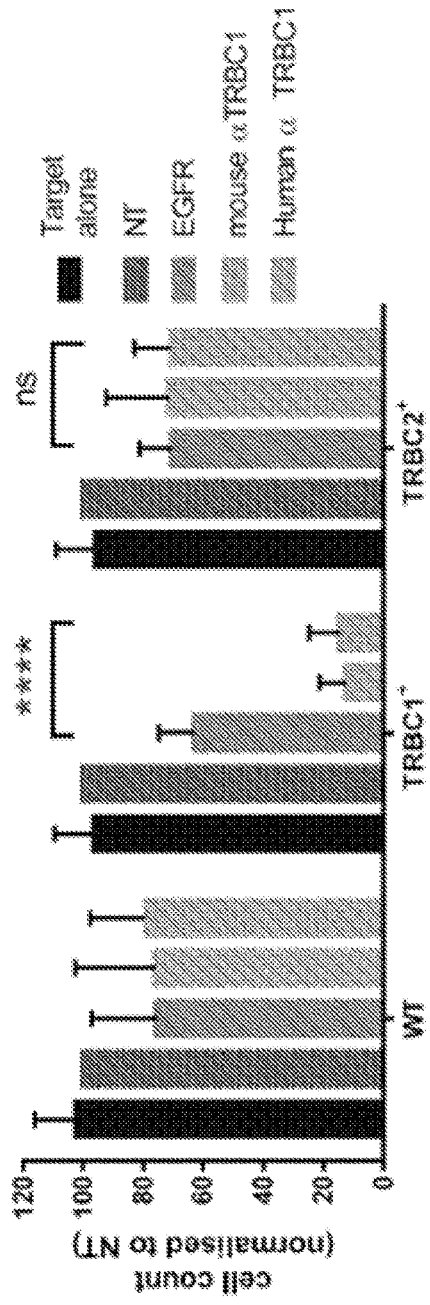
FIGS. 10A and 10B: CAR-mediated specific killing of TRBC1+targets. Untransfected T cells, or T cells expressing a murine anti-TRBC1 CAR (positive control); a humanised anti-TRBC1 CAR; or an anti-EGFRvIII CAR (negative control) were co-cultured with TRBC1-expressing or TRBC2-expressing Raji target cells and killing was analysed using flow cytometry.
Figure 10B:
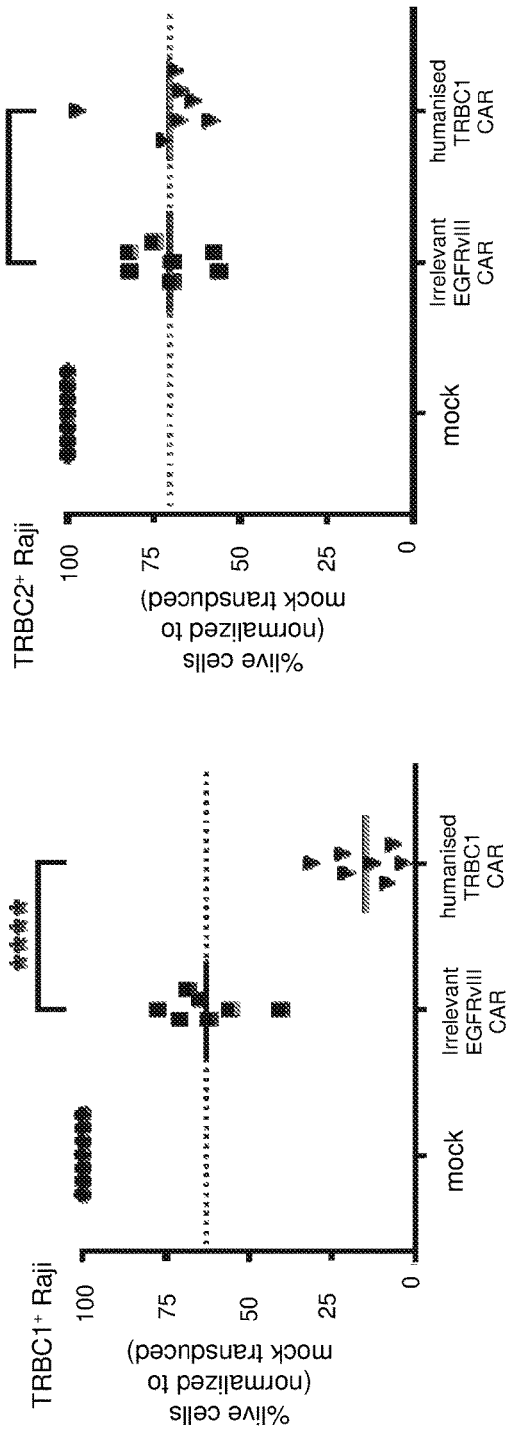
Figure 10B:
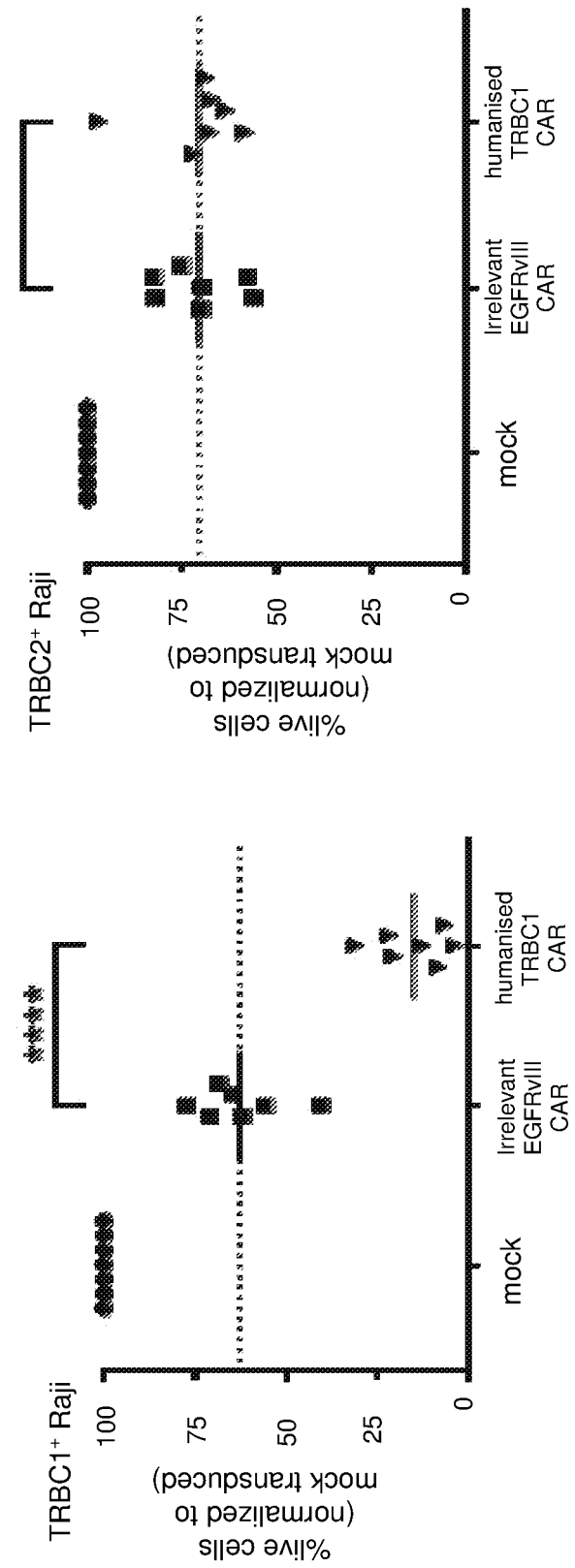

The results are shown in FIG. 10. T cells expressing the humanised TRBC1 CAR killed TRBC1-expressing but not TRBC2-expressing target cells.

Figure 11:
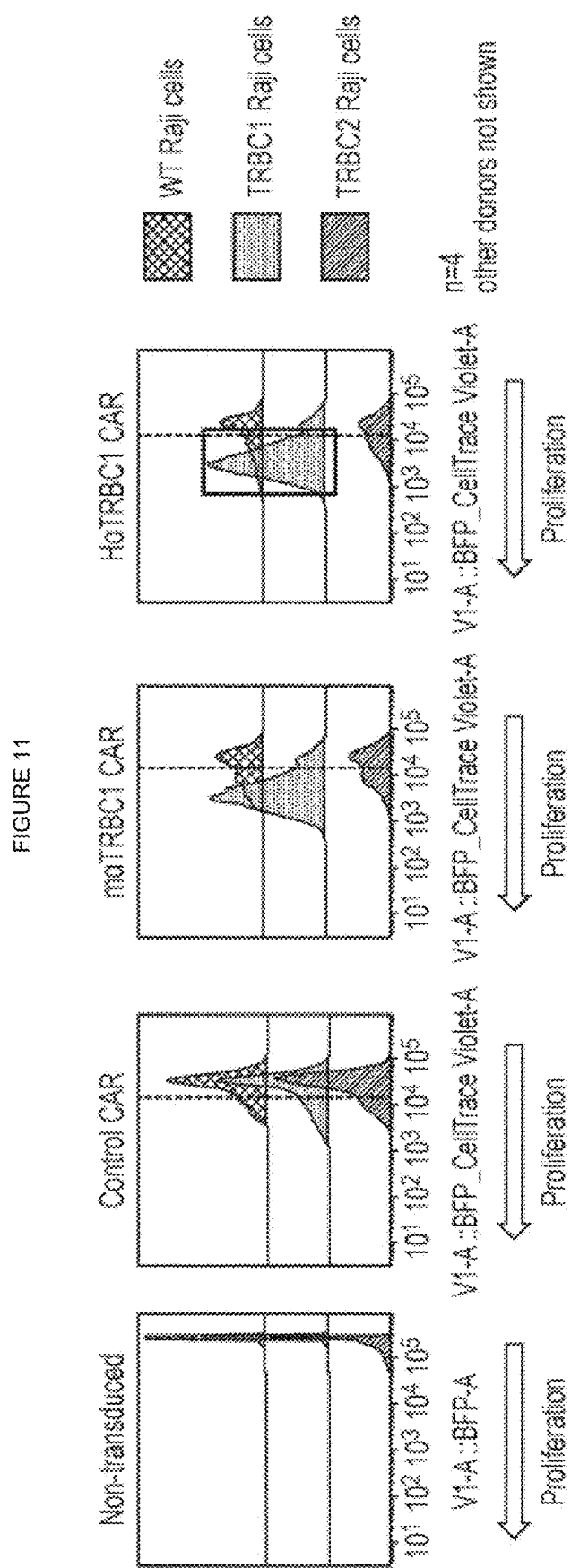
FIG. 11: Proliferation of CAR-expressing T cells following co-culture with target cells. Untransfected T cells, T cells expressing a murine anti-TRBC1 CAR; or T cells expressing a humanised anti-TRBC1 CAR; were co-cultured with TRBC1-expressing or TRBC2-expressing Raji target cells for 72 hours and T-cell proliferation was measured.

T cell proliferation was measured after 72 hours of co-culture with TRBC1- or TRBC2-expressing target cells and the results are shown in FIG. 11. T cells expressing either the murine Jovi-1 CAR or the humanised CAR showed an increase in proliferation when co-cultured with TRBC1-expressing, but not TRBC2-expressing target cells.

Figure 12:
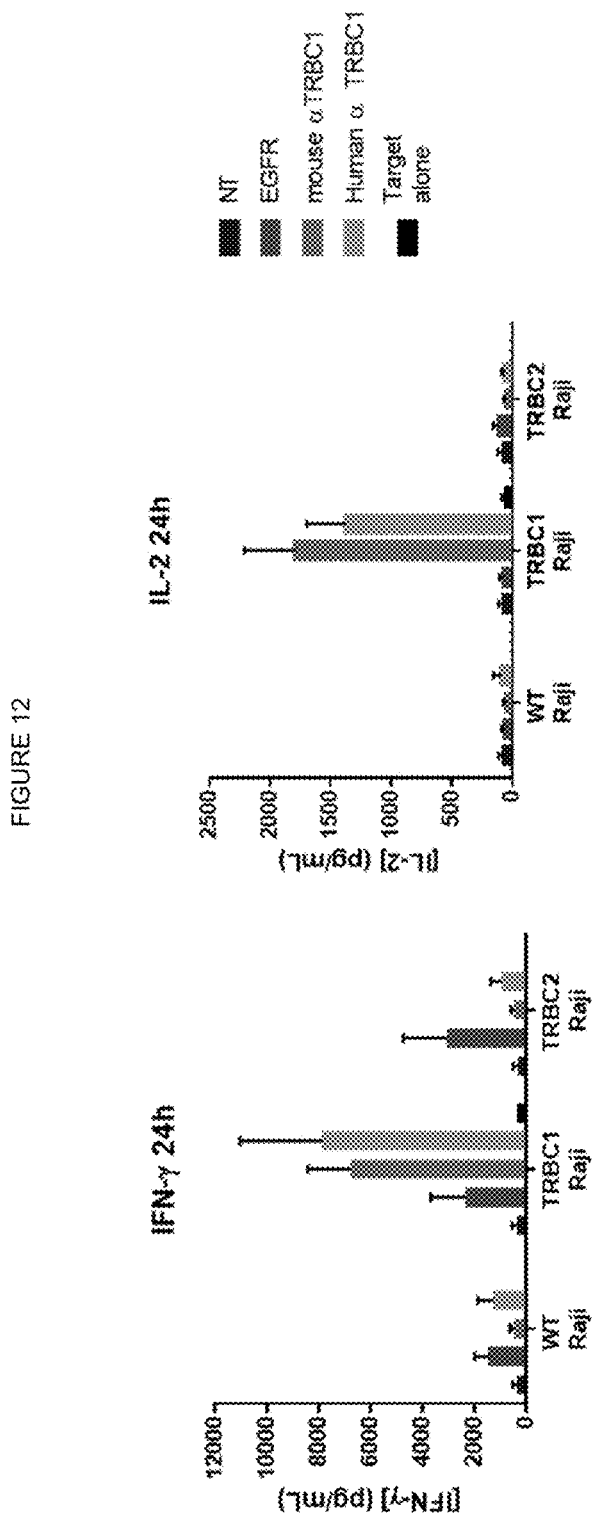
FIG. 12: Cytokine release following co-culture of CAR-expressing T cells and target cells. Untransfected T cells, or T cells expressing a murine anti-TRBC1 CAR (positive control); a humanised anti-TRBC1 CAR; or an anti-EGFRvIII CAR (negative control) were co-cultured with TRBC1-expressing or TRBC2-expressing Raji target cells. Release of IFNγ and IL-2 was measured after 24 hours.

Cytokine release was measured after 24 hours of co-culture with TRBC1- or TRBC2-expressing targets. The results are shown in FIG. 12. T cells expressing either the murine Jovi-1 CAR or the humanised CAR showed an increase in release of IFNγ and IL-2 when co-cultured with TRBC1-expressing, but not TRBC2-expressing target cells.

Example 5—Humanised αTRBC1 CAR Clears Tumour in NSG Mouse Model

Female NSG mice, age 7-8 weeks, were implanted with Jurkat cells transduced to express CD19-Fluc ($3 \times 10^6$ cells per animal in 0.1 ml PBS). On day 7, mice (n=8/group) received intravenous infusions of $1.0 \times 106$ aTRBC1 CAR T cells or mock-transduced cells (NT). Tumour growth was checked on study days 6, 9, 12 and 15 by bioluminescent imaging (BLI). Briefly, the mice were injected (s.c.) with 150 mg/kg D-Luciferin 15 minutes prior to imaging. 10 minutes following administration of D-Luciferin mice were anaesthetised and placed into the imaging chamber and imaged for luminescence (ventral view and dorsal view; up to 5 mice laid alongside each other in cage order). Duration and binning (sensitivity) of the image acquisition was captured and processed using Living Image 4.3.1 software.

Figure 13:
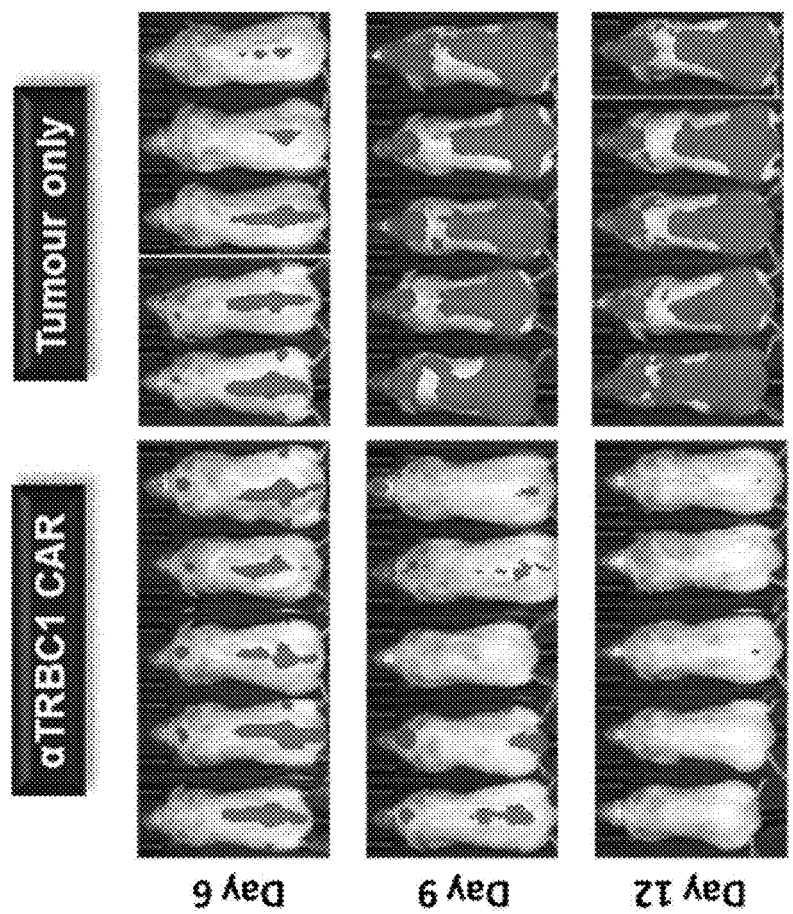
FIG. 13: Effect of humanised anti-TRBC1 CAR on tumour growth in an NSG mouse model

The results are shown in FIG. 13. By day 12, the humanised anti-TRBC1 CAR-T cells had cleared the tumour in all animals.

Example 6—Comparing the Effect of Murine and Humanised Anti-TRBC1 CAR T Cells on Exhaustion Activated PBMCs were transduced with vectors expressing the murine Jovi-1 CAR or a humanised Jovi-1 CAR which comprises the CDRs from JOVI-1 with H-AF062256 VH framework regions and 3aaz VL framework regions. Cells were collected after two days and maintained in culture medium with 50 U/mL IL-2 for a further two days. Transduced T cells were depleted of CD56-expressing cells using the EasySep CD56 positive selection kit. Co-cultures of TRBC1-TCR-expressing Raji targets with CAR T cells were carried out as follows: target cells were plated at 50,000 cells per well at effector:target ratio of 1:1 in 96-well U-bottom plates. After 96 hours, co-cultures were harvested and cells were stained with anti-PD1, anti-LAG3 and anti-Tim3 antibodies then analysed by flow cytometry.

The results are shown in FIG. 14. T cells expressing the humanised anti-TRBC1 CAR expressed lower levels of all three exhaustion markers than T cells expressing the murine CAR. This was true for both CD4+ and CD8+ T cells. T cells expressing the humanised CAR therefore surprisingly become less exhausted during exposure to target cells than T cells expressing a CAR with an scFv derived from the murine Jovi-1 antibody.

T cell exhaustion is a state of T cell dysfunction which arises during many chronic infections and cancer. It is defined by poor effector function. In order for a CAR-T cell to be efficient at killing target cells, it is advantageous to avoid or reduce the rate of T cell exhaustion.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

The invention claimed is:

1. A chimeric antigen receptor (CAR) comprising:
   a) an anti-T-cell Receptor β-constant region (TRBC)1 antigen binding domain comprising the heavy chain variable region domain of SEQ ID NO: 9 and the light chain variable region domain of SEQ ID NO: 19, and
   b) a 41BB-CD3zeta endodomain.

2. A nucleic acid encoding the CAR of claim 1.

3. A vector comprising the nucleic acid of claim 2.

4. A nucleic acid construct comprising a first nucleic acid encoding the CAR of claim 1 and a second nucleic acid encoding a suicide gene.

5. A vector comprising the nucleic acid construct of claim 4.

6. A T cell comprising the CAR of claim 1.

7. A method for making the T cell of claim 6 comprising the step of introducing into a T cell:
   a) a nucleic acid or vector encoding a CAR,
   b) a nucleic acid construct comprising a first nucleic acid encoding a CAR and a second nucleic acid encoding a suicide gene, or
   c) a vector comprising a nucleic acid construct according to b);
   wherein the CAR of a) and b) comprises an anti-TRBC1 antigen binding domain comprising the VH domain of SEQ ID NO: 9 and the VL domain of SEQ ID NO: 19, and a 41BB-CD3zeta endodomain.

8. A pharmaceutical composition comprising a plurality of T cells of claim 6 and a carrier, diluent or excipient.

9. A method of treating a TRBC1-expressing T-cell lymphoma or leukaemia in a subject comprising the step of administering the pharmaceutical composition of claim 8 to the subject.

10. The method of claim 9, wherein the TRBC1-expressing T-cell lymphoma or leukaemia is a peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia or T-cell acute lymphoblastic leukaemia.

* * * * *

UNITED STATES PATENT AND TRADEMARK OFFICE
CERTIFICATE OF CORRECTION

PATENT NO. : 11,434,293 B2
APPLICATION NO. : 17/499687
DATED : September 6, 2022
INVENTOR(S) : Shaun Cordoba et al.

It is certified that error appears in the above-identified patent and that said Letters Patent is hereby corrected as shown below:

On the Title Page

At item (63), Line 3, "2018." should be -- 2018, now Pat. No. 11,440,961. --.

Signed and Sealed this
Twenty-eighth Day of March, 2023

Katherine Kelly Vidal
Director of the United States Patent and Trademark Office

SEQUENCE LISTING

```
<160> NUMBER OF SEQ ID NOS: 36

<210> SEQ ID NO 1
<211> LENGTH: 7
<212> TYPE: PRT
<213> ORGANISM: Artificial Sequence
<220> FEATURE:
<223> OTHER INFORMATION: variable heavy chain (VH) complementarity
      determining region (CDR)1, VH CDR1

<400> SEQUENCE: 1

Gly Tyr Thr Phe Thr Gly Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: VH CDR2

<400> SEQUENCE: 2

Asn Pro Tyr Asn Asp Asp
1               5

<210> SEQ ID NO 3
<211> LENGTH: 15
<212> TYPE: PRT
<213> ORGANISM: Artificial Sequence
<220> FEATURE:
<223> OTHER INFORMATION: VH CDR3
```

```
<400> SEQUENCE: 3

Gly Ala Gly Tyr Asn Phe Asp Gly Ala Tyr Arg Phe Phe Asp Phe
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: variable light chain (VL) CDR1

<400> SEQUENCE: 4

Arg Ser Ser Gln Arg Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: VL CDR2

<400> SEQUENCE: 5

Arg Val Ser Asn Arg Phe Pro
1               5

<210> SEQ ID NO 6
<211> LENGTH: 9
<212> TYPE: PRT
<213> ORGANISM: Artificial Sequence
<220> FEATURE:
<223> OTHER INFORMATION: VL CDR3

<400> SEQUENCE: 6

Ser Gln Ser Thr His Val Pro Tyr Thr
1               5

<210> SEQ ID NO 7
<211> LENGTH: 124
<212> TYPE: PRT
<213> ORGANISM: Mus musculus

<400> SEQUENCE: 7

Glu Val Arg Leu Gln Gln Ser Gly Pro Asp Leu Ile Lys Pro Gly Ala
1               5                   10                  15

Ser Val Lys Met Ser Cys Lys Ala Ser Gly Tyr Thr Phe Thr Gly Tyr
            20                  25                  30

Val Met His Trp Val Lys Gln Arg Pro Gly Gln Gly Leu Glu Trp Ile
        35                  40                  45

Gly Phe Ile Asn Pro Tyr Asn Asp Asp Ile Gln Ser Asn Glu Arg Phe
    50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser Ser
        115                 120

<210> SEQ ID NO 8
```

<211> LENGTH: 113
<212> TYPE: PRT
<213> ORGANISM: Mus musculus

<400> SEQUENCE: 8

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

Arg

<210> SEQ ID NO 9
<211> LENGTH: 124
<212> TYPE: PRT
<213> ORGANISM: Artificial Sequence
<220> FEATURE:
<223> OTHER INFORMATION: humanised Jovi-1 H-AF062256 framework

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Met Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: humanised Jovi-1 H-EF177999 framework

<400> SEQUENCE: 10

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Val Met His Trp Val Arg Gln Ala Pro Gly Gln Gly Leu Glu Trp Met
            35                  40                  45

Gly Phe Ile Asn Pro Tyr Asn Asp Asp Ile Gln Ser Asn Glu Arg Phe
 50                  55                  60

Arg Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Ala Gly Tyr Asn Phe Asp Gly Ala Tyr Arg Phe Phe Asp
                100                 105                 110

Phe Trp Gly Gln Gly Thr Leu Val Thr Val Ser Ser
            115                 120

<210> SEQ ID NO 11
<211> LENGTH: 124
<212> TYPE: PRT
<213> ORGANISM: Artificial Sequence
<220> FEATURE:
<223> OTHER INFORMATION: humanised Jovi-1 H- H-KF688165 framework

<400> SEQUENCE: 11

Gln Val Gln Leu Val Gln Ser Gly Ala Glu Val Lys Lys Pro Gly Ala
 1               5                  10                  15

Ser Val Lys Val Ser Cys Lys Ala Ser Glu Tyr Ser Phe Thr Gly Tyr
                20                  25                  30

Val Met His Trp Val Arg Gln Ala Pro Gly Gln Gly Leu Glu Trp Met
            35                  40                  45

Gly Phe Ile Asn Pro Tyr Asn Asp Asp Ile Gln Ser Asn Glu Arg Phe
 50                  55                  60

Arg Gly Arg Val Thr Met Thr Arg Asp Thr Ser Ile Ser Thr Ala Tyr
 65                  70                  75                  80

Met Glu Val Ser Ser Leu Thr Ser Asp Asp Ala Ala Ile Tyr Tyr Cys
                85                  90                  95

Ala Arg Gly Ala Gly Tyr Asn Phe Asp Gly Ala Tyr Arg Phe Phe Asp
                100                 105                 110

Phe Trp Gly Gln Gly Thr Leu Val Thr Val Ser Ser
            115                 120

<210> SEQ ID NO 12
<211> LENGTH: 124
<212> TYPE: PRT
<213> ORGANISM: Artificial Sequence
<220> FEATURE:
<223> OTHER INFORMATION: variable heavy chain (VH) sequence with
      back-mutation, mutation K73

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Val Met His Trp Val Arg Gln Ala Pro Gly Gln Gly Leu Glu Trp Met
            35                  40                  45

Gly Phe Ile Asn Pro Tyr Asn Asp Asp Ile Gln Ser Asn Glu Arg Phe
 50                  55                  60

Arg Gly Arg Val Thr Met Thr Arg Asp Lys Ser Ile Ser Thr Ala Tyr
 65                  70                  75                  80

Met Glu Leu Ser Arg Leu Arg Ser Asp Asp Thr Ala Val Tyr Tyr Cys

```
                    85                  90                  95

Ala Arg Gly Ala Gly Tyr Asn Phe Asp Gly Ala Tyr Arg Phe Phe Asp
            100                 105                 110

Phe Trp Gly Gln Gly Thr Met Val Thr Val Ser Ser
        115                 120
```

<210> SEQ ID NO 13
<211> LENGTH: 124
<212> TYPE: PRT
<213> ORGANISM: Artificial Sequence
<220> FEATURE:
<223> OTHER INFORMATION: VH sequence with back-mutation, mutation S71

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Val Met His Trp Val Arg Gln Ala Pro Gly Gln Gly Leu Glu Trp Met
            35                  40                  45

Gly Phe Ile Asn Pro Tyr Asn Asp Asp Ile Gln Ser Asn Glu Arg Phe
        50                  55                  60

Arg Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Met Val Thr Val Ser Ser
        115                 120
```

<210> SEQ ID NO 14
<211> LENGTH: 124
<212> TYPE: PRT
<213> ORGANISM: Artificial Sequence
<220> FEATURE:
<223> OTHER INFORMATION: VH sequence with back-mutation, mutations S71, K73

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Val Met His Trp Val Arg Gln Ala Pro Gly Gln Gly Leu Glu Trp Met
            35                  40                  45

Gly Phe Ile Asn Pro Tyr Asn Asp Asp Ile Gln Ser Asn Glu Arg Phe
        50                  55                  60

Arg Gly Arg Val Thr Met Thr Ser Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Met Val Thr Val Ser Ser
        115                 120
```

<210> SEQ ID NO 15

```
<211> LENGTH: 124
<212> TYPE: PRT
<213> ORGANISM: Artificial Sequence
<220> FEATURE:
<223> OTHER INFORMATION: VH sequence with back-mutation, mutation I48

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Val Met His Trp Val Arg Gln Ala Pro Gly Gln Gly Leu Glu Trp Ile
            35                  40                  45

Gly Phe Ile Asn Pro Tyr Asn Asp Asp Ile Gln Ser Asn Glu Arg Phe
        50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Met Val Thr Val Ser Ser
        115                 120

<210> SEQ ID NO 16
<211> LENGTH: 124
<212> TYPE: PRT
<213> ORGANISM: Artificial Sequence
<220> FEATURE:
<223> OTHER INFORMATION: VH sequence with back-mutation, mutations I48,
      K73

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Val Met His Trp Val Arg Gln Ala Pro Gly Gln Gly Leu Glu Trp Ile
            35                  40                  45

Gly Phe Ile Asn Pro Tyr Asn Asp Asp Ile Gln Ser Asn Glu Arg Phe
        50                  55                  60

Arg Gly Arg Val Thr Met Thr Arg Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Met Val Thr Val Ser Ser
        115                 120

<210> SEQ ID NO 17
<211> LENGTH: 124
<212> TYPE: PRT
<213> ORGANISM: Artificial Sequence
<220> FEATURE:
<223> OTHER INFORMATION: VH sequence with back-mutation, mutations M20,
      S71, K73

<400> SEQUENCE: 17

Gln Val Gln Leu Val Gln Ser Gly Ala Glu Val Lys Lys Pro Gly Ala
```

```
1               5                   10                  15
Ser Val Lys Met Ser Cys Lys Ala Ser Gly Tyr Thr Phe Thr Gly Tyr
            20                  25                  30

Val Met His Trp Val Arg Gln Ala Pro Gly Gln Gly Leu Glu Trp Met
            35                  40                  45

Gly Phe Ile Asn Pro Tyr Asn Asp Asp Ile Gln Ser Asn Glu Arg Phe
        50                  55                  60

Arg Gly Arg Val Thr Met Thr Ser Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
                100                 105                 110

Phe Trp Gly Gln Gly Thr Met Val Thr Val Ser Ser
            115                 120

<210> SEQ ID NO 18
<211> LENGTH: 124
<212> TYPE: PRT
<213> ORGANISM: Artificial Sequence
<220> FEATURE:
<223> OTHER INFORMATION: VH sequence with back-mutation, mutations M20,
      I48

<400> SEQUENCE: 18

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Gly Tyr
            20                  25                  30

Val Met His Trp Val Arg Gln Ala Pro Gly Gln Gly Leu Glu Trp Ile
            35                  40                  45

Gly Phe Ile Asn Pro Tyr Asn Asp Asp Ile Gln Ser Asn Glu Arg Phe
        50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ala Gly Tyr Asn Phe Asp Gly Ala Tyr Arg Phe Phe Asp
                100                 105                 110

Phe Trp Gly Gln Gly Thr Met Val Thr Val Ser Ser
            115                 120

<210> SEQ ID NO 19
<211> LENGTH: 112
<212> TYPE: PRT
<213> ORGANISM: Artificial Sequence
<220> FEATURE:
<223> OTHER INFORMATION: JOVI-1 VL CDRs with the human framework 3aaz

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: variable light chain (VL) sequence with
      back-mutations

<400> SEQUENCE: 20

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Arg Leu Val His Ser
                20                  25                  30

Asn Gly Asn Thr Tyr Leu His Trp Tyr Leu Gln Lys Pro Gly Gln Ser
            35                  40                  45

Pro Arg Leu Leu Ile Tyr Arg Val Ser Asn Arg Phe Pro Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 21

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Arg Leu Val His Ser
                20                  25                  30

Asn Gly Asn Thr Tyr Leu His Trp Tyr Leu Gln Lys Pro Gly Gln Ser
            35                  40                  45

Pro Arg Leu Leu Ile Tyr Arg Val Ser Asn Arg Phe Pro Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 22
<211> LENGTH: 112
<212> TYPE: PRT
<213> ORGANISM: Artificial Sequence
<220> FEATURE:

<223> OTHER INFORMATION: VL sequence with back-mutations

<400> SEQUENCE: 22

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 23

Asp Ile Val Met Thr Gln Ser Pro Leu Ser Leu Pro Val Thr Leu Gly
1               5                   10                  15

Glu Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 24

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Phe Cys Ser Gln Ser
                    85                  90                  95

Thr His Val Pro Tyr Thr Phe Gly Gly Gly Thr Lys Leu Glu Ile Lys
                100                 105                 110

<210> SEQ ID NO 25
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 25

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Arg Leu Val His Ser
                20                  25                  30

Asn Gly Asn Thr Tyr Leu His Trp Tyr Leu Gln Lys Pro Gly Gln Ser
            35                  40                  45

Pro Arg Leu Leu Ile Tyr Arg Val Ser Asn Arg Phe Pro Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Ser Gln Ser
                85                  90                  95

Thr His Val Pro Tyr Thr Phe Gly Gln Gly Thr Lys Leu Glu Ile Lys
                100                 105                 110

<210> SEQ ID NO 26
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 26

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Arg Leu Val His Ser
                20                  25                  30

Asn Gly Asn Thr Tyr Leu His Trp Tyr Leu Gln Lys Pro Gly Gln Ser
            35                  40                  45

Pro Arg Leu Leu Ile Tyr Arg Val Ser Asn Arg Phe Pro Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Leu Glu Ile Lys
                100                 105                 110

<210> SEQ ID NO 27
<211> LENGTH: 112
<212> TYPE: PRT
<213> ORGANISM: Artificial Sequence
<220> FEATURE:
<223> OTHER INFORMATION: VL sequence with back-mutation

<400> SEQUENCE: 27
```

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 28

```
Asp Ile Val Met Thr Gln Ser Pro Leu Ser Leu Pro Val Thr Pro Gly
1               5                   10                  15

Glu Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 29
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 29

```
Asp Ile Val Met Thr Gln Ser Pro Leu Ser Leu Pro Val Thr Pro Gly
1               5                   10                  15

Glu Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
```

```
                    85                  90                  95

Thr His Val Pro Tyr Thr Phe Gly Gln Gly Thr Lys Leu Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 30

Asp Ile Val Met Thr Gln Ser Pro Leu Ser Leu Pro Val Thr Pro Gly
1               5                   10                  15

Glu Gln Ala Ser Ile Ser Cys Arg Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: VL sequence with back-mutation

<400> SEQUENCE: 31

Asp Ile Val Met Thr Gln Ser Pro Leu Ser Leu Pro Val Thr Pro Gly
1               5                   10                  15

Glu Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: VL sequence with back-mutations

<400> SEQUENCE: 32

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: VL sequence with back-mutation

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: VL sequence with back-mutation

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Leu Glu Ile Lys

<210> SEQ ID NO 35
<211> LENGTH: 175
<212> TYPE: PRT
<213> ORGANISM: Homo sapiens

<400> SEQUENCE: 35

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp
                165                 170                 175

<210> SEQ ID NO 36
<211> LENGTH: 175
<212> TYPE: PRT
<213> ORGANISM: Homo sapiens

<400> SEQUENCE: 36

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

```
Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp
                165                 170                 175
```